United States Patent
Yedgar

(10) Patent No.: US 11,911,507 B2
(45) Date of Patent: *Feb. 27, 2024

(54) LIPOSOMES COMPRISING POLYMER-CONJUGATED LIPIDS AND RELATED USES

(71) Applicant: Yissum Research Development Company of the Hebrew University of Jerusalem Ltd., Jerusalem (IL)

(72) Inventor: Saul Yedgar, Jerusalem (IL)

(73) Assignee: Yissum Research Development Company of the Hebrew University of Jerusalem Ltd., Jerusalem (IL)

(*) Notice: Subject to any disclaimer, the term of this patent is extended or adjusted under 35 U.S.C. 154(b) by 47 days.

This patent is subject to a terminal disclaimer.

(21) Appl. No.: 17/377,134

(22) Filed: Jul. 15, 2021

(65) Prior Publication Data

US 2021/0338582 A1 Nov. 4, 2021

Related U.S. Application Data

(63) Continuation of application No. 16/853,635, filed on Apr. 20, 2020, now abandoned, which is a continuation of application No. 16/246,920, filed on Jan. 14, 2019, now Pat. No. 10,624,851, which is a continuation of application No. 14/115,869, filed as application No. PCT/IL2012/050168 on May 10, 2012, now Pat. No. 10,179,106.

(60) Provisional application No. 61/485,192, filed on May 12, 2011.

(51) Int. Cl.
*A61K 9/127* (2006.01)
*A61K 31/713* (2006.01)
*A61K 47/69* (2017.01)

(52) U.S. Cl.
CPC ............ *A61K 9/127* (2013.01); *A61K 9/1271* (2013.01); *A61K 31/713* (2013.01); *A61K 47/6911* (2017.08)

(58) Field of Classification Search
None
See application file for complete search history.

(56) References Cited

U.S. PATENT DOCUMENTS

| | | | |
|---|---|---|---|
| 5,395,619 A | 3/1995 | Zalipsky et al. | |
| 5,785,975 A | 7/1998 | Parikh | |
| 10,179,106 B2* | 1/2019 | Yedgar | A61K 31/713 |
| 10,624,851 B2* | 4/2020 | Yedgar | A61K 47/6911 |
| 2004/0071768 A1 | 4/2004 | Sarris et al. | |
| 2004/0241855 A1* | 12/2004 | Cullis | A61K 48/00 525/54.1 |
| 2005/0276756 A1 | 12/2005 | Hoo et al. | |
| 2007/0185052 A1 | 8/2007 | Yedgar et al. | |
| 2010/0209490 A1 | 8/2010 | Morita et al. | |

FOREIGN PATENT DOCUMENTS

| | | |
|---|---|---|
| WO | 2001/51003 A2 | 7/2001 |
| WO | 2005/084307 A2 | 3/2004 |
| WO | 2011/017297 A2 | 2/2011 |

OTHER PUBLICATIONS

International Search Report of Application No. PCT/IL2012/050168 dated Jan. 25, 2013.
Mozafari et al. Nanoliposomes and their Applications in Food Nanotechnology. J. Liposome; Res. 2008; 18(4):309-27.

* cited by examiner

*Primary Examiner* — Melissa S Mercier
(74) *Attorney, Agent, or Firm* — Edell, Shapiro & Finnan, LLC

(57) ABSTRACT

The present invention provides liposomes comprising a lipid bilayer and a polymer-conjugated lipid, wherein said polymer-conjugated lipid is incorporated into said lipid bilayer. The present invention also provides methods of producing the liposomes as well as a method of delivering a nucleic acid to a subject comprising the step of administering said nucleic acid encapsulated in a mixed liposome, a method for performing diagnostic imaging in a subject, comprising the step of administering a diagnostic agent encapsulated in a mixed liposome, and methods for treating, inhibiting, or suppressing a pathological condition in a subject comprising administering to said subject a mixed liposome.

17 Claims, 3 Drawing Sheets

US 11,911,507 B2

LIPOSOMES COMPRISING POLYMER-CONJUGATED LIPIDS AND RELATED USES

CROSS-REFERENCE TO RELATED APPLICATIONS

This application is a continuation of application Ser. No. 16/853,635, filed Apr. 20, 2020, which is a continuation of application Ser. No. 16/246,920, filed Feb. 7, 2014, issued as U.S. Pat. No. 10,624,851, on Apr. 21, 2020, which is a continuation of application Ser. No. 14/115,869, filed Feb. 7, 2014, issued as U.S. Pat. No. 10,179,106, on Jan. 15, 2019, which is a National Phase Application of PCT International Application No. PCT/IL2012/050168, International Filing Date May 10, 2012, which claims priority to U.S. Provisional Patent Application No. 61/485,192, filed May 12, 2011, the contents of each of which are hereby incorporated by reference in their entireties.

FIELD OF THE INVENTION

The present invention provides liposomes comprising a lipid bilayer and a polymer-conjugated lipid, wherein said polymer-conjugated lipid is incorporated into said lipid bilayer. The present invention also provides methods of producing the liposomes as well as a method of delivering a nucleic acid to a subject comprising the step of administering said nucleic acid encapsulated in a mixed liposome, a method for performing diagnostic imaging in a subject, comprising the step of administering a diagnostic agent encapsulated in a mixed liposome, and methods for treating, inhibiting, or suppressing a pathological condition in a subject comprising administering to said subject a mixed liposome.

BACKGROUND OF THE INVENTION

The use of drug delivery systems providing both slow release of drugs and specific targeting of drugs to the desired affected organs/systems in order to reduce systemic distribution and exposure of non-target organs has long been sought. One promising candidate has been phospholipid (PL) liposomes and their derivatives. Liposomes are small, spherical vesicles composed of phospholipids and consist of one or more lipid bilayers enclosing an aqueous interior. Liposomes can encapsulate both hydrophilic drugs (in the aqueous interior) and lipophilic drugs (in the lipid bilayer), and arm thus highly suitable for drug delivery.

Phospholipid liposomes can serve as sustained-release or controlled-release drug depots, thus contributing to improvement in drug efficacy and allowing reduction in the frequency of dosing. By providing protection of both the entrapped drug and the biological environment, liposomes reduce the risks of drug inactivation and drug degradation. Since the pharmacokinetics of free drug release from the particles are different from directly-administered free drug, these carriers can be used to reduce toxicity and undesirable side effects.

Phospholipid liposomes can be prepared at a wide range of sizes (50-500 nm). Since in inflamed tissues, the intercellular space is enlarged from the normal distance of 50 nm to 100 nm, drug-carrying liposomes smaller than 100 nm are suitable for selective delivery of drugs to target systems.

Despite the advantages offered, there are some difficulties associated with using drug encapsulating liposomes. For example, liposomes have limited targeting abilities, limited retention and stability in circulation, potential toxicity upon chronic administration, and the inability to extravasate.

To circumvent the drawbacks of known nanoliposomes, we have used polymer-conjugated lipids (Po-Ls) for the formation of mixed lipid/Po-L nanoliposomes.

SUMMARY OF THE INVENTION

In one embodiment, the present invention provides a liposome comprising a lipid bilayer and a polymer-conjugated lipid, wherein said polymer-conjugated lipid is incorporated into said lipid bilayer.

In another embodiment, the present invention provides a liposome comprising a lipid bilayer and a glycosaminoglycan (GAG)-conjugated lipid, wherein said polymer-conjugated lipid is incorporated into said lipid bilayer.

In another embodiment, the present invention provides a liposome comprising a lipid bilayer and a polymer-conjugated lipid, wherein said polymer-conjugated lipid is incorporated into said lipid bilayer and wherein said polymer is not a glycosaminoglycan.

In another embodiment, the present invention provides a method of producing a mixed liposome comprising the step of conjugating a lipid with a polymer to form a polymer-conjugated lipid and contacting said polymer-conjugated lipid with a liposome to produce a mixed liposome.

In another embodiment, the present invention provides a mixed liposome produced by the method comprising the step of conjugating a lipid with a polymer to form a polymer-conjugated lipid and contacting said polymer-conjugated lipid with a liposome to produce a mixed liposome.

In another embodiment, the present invention provides a composition comprising a liposome comprising a lipid bilayer and a polymer-conjugated lipid, wherein said polymer-conjugated lipid is incorporated into said lipid bilayer.

In another embodiment, the present invention provides a composition comprising a liposome comprising a lipid bilayer and a glycosaminoglycan (GAG)-conjugated lipid, wherein said polymer-conjugated lipid is incorporated into said lipid bilayer.

In another embodiment, the present invention provides a composition comprising a liposome comprising a lipid bilayer and a polymer-conjugated lipid, wherein said polymer-conjugated lipid is incorporated into said lipid bilayer and wherein said polymer is not a glycosaminoglycan.

In another embodiment, the present invention provides a drug delivery system comprising a liposome comprising a lipid bilayer and a polymer-conjugated lipid, wherein said polymer-conjugated lipid is incorporated into said lipid bilayer.

In another embodiment, the present invention provides a method of delivering a nucleic acid to a subject comprising the step of administering said nucleic acid encapsulated in a liposome comprising a lipid bilayer and a polymer-conjugated lipid, wherein said polymer-conjugated lipid is incorporated into said lipid bilayer to said subject.

In another embodiment, the present invention provides a method for performing diagnostic imaging in a subject, comprising the step of administering a diagnostic agent encapsulated in a liposome comprising a lipid bilayer and a polymer-conjugated lipid, wherein said polymer-conjugated lipid is incorporated into said lipid bilayer to said subject and imaging said patient.

In another embodiment, the present invention provides a method for treating, inhibiting, or suppressing a pathological condition in a subject, comprising administering to said subject a liposome comprising a lipid bilayer and a polymer-conjugated lipid, wherein said polymer-conjugated lipid is incorporated into said lipid bilayer.

BRIEF DESCRIPTION OF THE DRAWINGS

The subject matter regarded as the invention is particularly pointed out and distinctly claimed in the concluding portion of the specification. The invention, however, may best be understood by reference to the following detailed description when read with the accompanying drawings.

DETAILED DESCRIPTION OF THE PRESENT INVENTION

Figure 1:
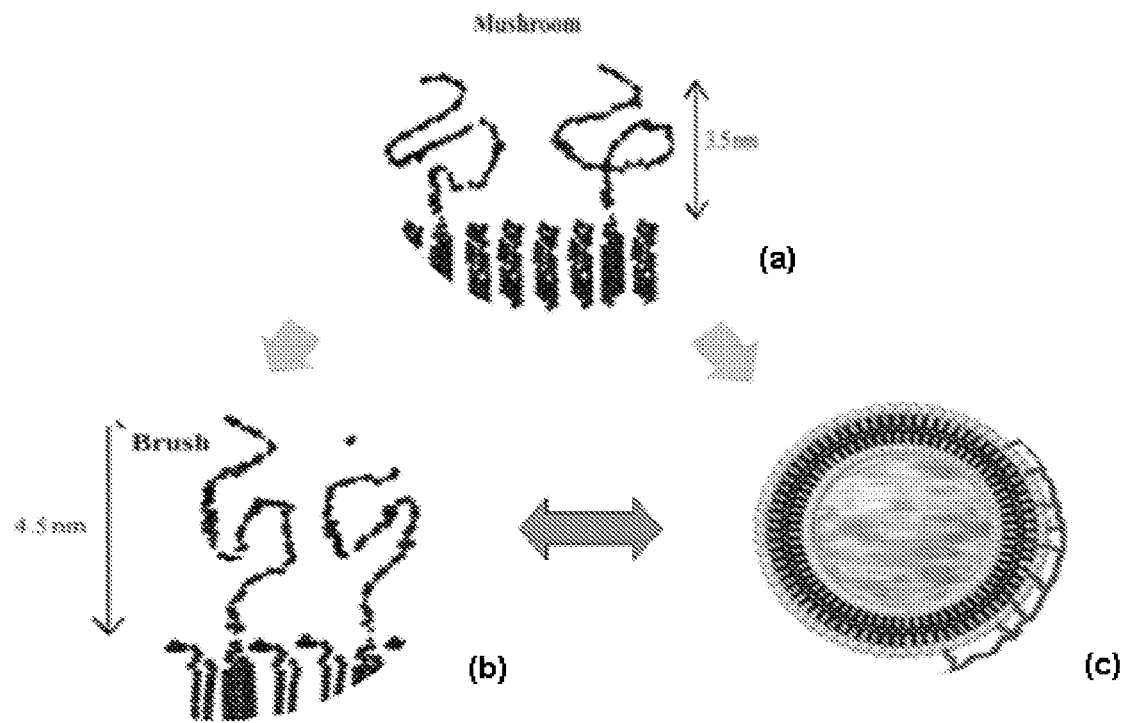
FIG. 1: Models representing how variations in polymer-conjugated lipid (Po-L)/liposome ratio and polymer size affect structure and function of Po-L/liposomes: (a) Mushroom: obtained at lower Po-L/liposome ratio. (b) Brush, obtained at higher Po-L/liposome ratio (c) Surface coating, obtained with high MW HA (or other GAGs).

A nanoliposome, or submicron bilayer lipid vesicle, is a technology for the encapsulation and delivery of bioactive agents. The list of bioactive material that can be incorporated to nanoliposomes is immense, ranging from pharmaceuticals to cosmetics and nutraceuticals. Because of their biocompatibility and biodegradability, along with their nanosize, nanoliposomes have potential applications in a vast range of fields, including nanotherapy (e.g. diagnosis, cancer therapy, gene delivery), cosmetics, food technology and agriculture. Nanoliposomes are able to enhance the performance of bioactive agents by improving their solubility and bioavailability, in vitro and in vivo stability, as well as preventing their unwanted interactions with other molecules. Another advantage of nanoliposomes is cell-specific targeting, which is a prerequisite to attain drug concentrations required for optimum therapeutic efficacy in the target site while minimizing adverse effects on healthy cells and tissues.

Polymer-Conjugated Lipid (Pol-L) Liposomes

In one embodiment, the present invention provides a liposome comprising a lipid bilayer and a polymer-conjugated lipid, wherein said polymer-conjugated lipid is incorporated into said lipid bilayer.

In one embodiment, the liposome is made from a first lipid while the lipid of the polymer-conjugated lipid(s) is made from a second lipid which is a different lipid from said first lipid. For example, and in one embodiment, the liposomes may be made using phosphatidylcholine, with or without cholesterol, while the conjugate may be made using phosphatidylethanolamine. In one embodiment, the polymer is a polysaccharide. In one embodiment, the polysaccharide is a glycosaminoglycan.

In one embodiment, said polymer is conjugated to said lipid via a covalent bond. In one embodiment, said polymer is cross-linked to said lipid.

In one embodiment, the present invention provides a liposome comprising two or more polymer-conjugated lipids, wherein said polymer-conjugated lipid comprises two or more lipids conjugated to a single polymer.

In one embodiment, the polymer-conjugated lipid is an inhibitor of phospholipase A2, or in another embodiment, the polymer-conjugated lipid inhibits the activity, function, or expression of phospholipase A2.

In one embodiment, the polymer is alginic acid. In one embodiment, the alginic acid is low molecular weight alginic acid. In another embodiment, the alginic acid is truncated.

In another embodiment, the present invention provides a liposome comprising a lipid bilayer and a glycosaminoglycan (GAG)-conjugated lipid, wherein said polymer-conjugated lipid is incorporated into said lipid bilayer.

In another embodiment, the present invention provides a liposome comprising two or more glycosaminoglycan (GAG)-conjugated lipids, wherein said GAG-conjugated lipid comprises two or more lipids conjugated to a single GAG.

In another embodiment, the present invention provides a liposome comprising two or more glycosaminoglycan (GAG)-conjugated phospholipids, wherein said GAG-conjugated phospholipid comprises two or more phospholipids conjugated to a single GAG.

In one embodiment, the GAG is hyaluronic acid. In one embodiment, the hyaluronic acid is low molecular weight hyaluronic acid. In another embodiment, the hyaluronic acid is truncated.

In another embodiment, the present invention provides a liposome comprising two or more low molecular weight hyaluronic acid-conjugated phosphatidylethanolamine, wherein said low molecular weight hyaluronic acid-conjugated phosphatidylethanolamine comprises two or more hyaluronic acid-conjugated phosphatidylethanolamines conjugated to a single hyaluronic acid.

In another embodiment, the present invention provides a liposome comprising a lipid bilayer and a polymer-conjugated lipid, wherein said polymer-conjugated lipid is incorporated into said lipid bilayer and wherein said polymer is not a glycosaminoglycan.

In another embodiment, the present invention provides a liposome comprising a polymer-conjugated lipid, wherein said polymer is not a glycosaminoglycan. In another embodiment, the present invention provides a liposome comprising a polymer-conjugated lipid, wherein said polymer is not hyaluronic acid.

In one embodiment, the polymer is a polysaccharide. In one embodiment, the lipid is a phospholipid. In one embodiment, the liposome comprises a lipid bilayer. In one embodiment, the polymer-conjugated lipid is incorporated into the lipid bilayer of the liposome. In one embodiment, the liposome is a modified liposome.

In one embodiment, the liposome is a nanoliposome. In one embodiment, the liposome is less than 100 nm in diameter. In another embodiment, the liposome is less than 150 nm in diameter. In another embodiment, the liposome is less than 75 nm in diameter. In another embodiment, the liposome is less than 50 nm in diameter. In another embodiment, the liposome is 1-100 nm in diameter. In another embodiment, the liposome is 20-100 nm in diameter. In another embodiment, the liposome is 50-100 nm in diameter. In another embodiment, the liposome is 50-150 nm in diameter. In another embodiment, the liposome is 20-150 nm in diameter. In another embodiment, the liposome is 10-50 nm in diameter.

In one embodiment, the liposome comprises a lipid bilayer and said polymer-conjugated lipid is incorporated into both the inner and outer leaflets of said lipid bilayer. In another embodiment, the liposome comprises a lipid bilayer and said polymer-conjugated lipid is incorporated only into the outer leaflet of said lipid bilayer. In another embodiment, the liposome comprises a lipid bilayer and said polymer-conjugated lipid is incorporated only into the inner leaflet of said lipid bilayer.

In another embodiment, Po-L liposomes of the present invention provide liposomes that are unusually stable. In one embodiment, Po-L liposomes of the present invention are inserted symmetrically to both the inner and outer leaflets of the liposome, i.e., having the polymer at both liposome surfaces, which in one embodiment, increases the liposome stability compared to the stability of the liposome when a small polymer is inserted only on the outer surface (leaflet) of the liposome. In one embodiment, insertion of a large polymer to only the outer liposome surface creates excessive asymmetry in the liposome and compromises the liposome stability.

In another embodiment, the present invention provides a modified liposome comprising a lipid bilayer, wherein said liposome comprises two or more polysaccharide-conjugated phospholipids (PoS-PLs) incorporated into said lipid bilayer.

In one embodiment, a liposome of the present invention is a modified liposome in that the liposome incorporates a polymer-conjugated lipid as described herein into its lipid bilayer, which in one embodiment, is comprised of a different lipid that the lipid of the polymer-conjugated lipid. In one embodiment, a modified liposome of the present invention is referred to as a mixed liposome.

In another embodiment, the present invention provides a modified liposome comprising a lipid bilayer, wherein said liposome comprises a polysaccharide-conjugated phospholipid (PoS-PL) incorporated into said lipid bilayer, wherein said polysaccharide is a glycosaminoglycan.

In another embodiment, the present invention provides a modified liposome comprising a lipid bilayer, wherein said liposome comprises a polysaccharide-conjugated phospholipid (PoS-PL) incorporated into said lipid bilayer, wherein said polysaccharide is a low molecular weight glycosaminoglycan.

In another embodiment, the present invention provides a modified liposome comprising a lipid bilayer, wherein said liposome comprises a polysaccharide-conjugated phospholipid (PoS-PL) incorporated into said lipid bilayer, wherein said polysaccharide is not a glycosaminoglycan.

In one embodiment, the present invention provides liposomes comprising polymer-conjugated lipids. In another embodiment, the present invention provides micelles comprising polymer-conjugated lipids. In another embodiment, the present invention provides nanoliposomes comprising polymer-conjugated lipids. In another embodiment, the present invention provides archaeosomes comprising polymer-conjugated lipids. In another embodiment, the present invention provides immunoliposomes comprising polymer-conjugated lipids. In another embodiment, the present invention provides virosomes comprising polymer-conjugated lipids. In another embodiment, the present invention provides ultradeformable vesicles comprising polymer-conjugated lipids. In another embodiment, the present invention provides stealth liposomes comprising polymer-conjugated lipids. In one embodiment, the polymer is a polysaccharide.

In one embodiment, the polymer-conjugated lipid comprises two or more lipids conjugated to a single polymer.

In one embodiment, the ratio of lipids to repeating polymer units in said polymer-conjugated lipid is between 1:2 and 1:1000. In another embodiment, the ratio of lipids to repeating polymer units in said polymer-conjugated lipid is between 2:4 and 2:2000. In another embodiment, the ratio of lipids to repeating polymer units in said polymer-conjugated lipid is between 1:28 and 1:62. In another embodiment, the ratio of lipids to repeating polymer units in said polymer-conjugated lipid is between 1:100 and 1:500. In another embodiment, the ratio of lipids to repeating polymer units in said polymer-conjugated lipid is between 1:25 and 1:35. In another embodiment, the ratio of lipids to repeating polymer units in said polymer-conjugated lipid is between 1:55 and 1:65. In another embodiment, the ratio of lipids to repeating polymer units in said polymer-conjugated lipid is between 1:20 and 1:70. In another embodiment, the ratio of lipids to repeating polymer units in said polymer-conjugated lipid is between 1:10 and 1:100. In another embodiment, the ratio of lipids to repeating polymer units in said polymer-conjugated lipid is between 1:50 and 1:500. In another embodiment, the ratio of lipids to repeating polymer units in said polymer-conjugated lipid is under 1:100.

In one embodiment, the ratio of repeating polymer units to lipids in said polymer-conjugated lipid is between 20 and 70. In another embodiment, the ratio of repeating polymer units to lipids in said polymer-conjugated lipid is between 28 and 62. In another embodiment, the ratio of repeating polymer units to lipids in said polymer-conjugated lipid is between 10 and 80. In another embodiment, the ratio of repeating polymer units to lipids in said polymer-conjugated lipid is approximately 30. In another embodiment, the ratio of repeating polymer units to lipids in said polymer-conjugated lipid is 28. In another embodiment, the ratio of repeating polymer units to lipids in said polymer-conjugated lipid is 25-30. In another embodiment, the ratio of repeating polymer units to lipids in said polymer-conjugated lipid is 20-35. In another embodiment, the ratio of repeating polymer units to lipids in said polymer-conjugated lipid is 15-40. In another embodiment, the ratio of repeating polymer units to lipids in said polymer-conjugated lipid is approximately 60. In another embodiment, the ratio of repeating polymer units to lipids in said polymer-conjugated lipid is 62. In another embodiment, the ratio of repeating polymer units to lipids in said polymer-conjugated lipid is 60-65. In another embodiment, the ratio of repeating polymer units to lipids in said polymer-conjugated lipid is 55-70. In another embodiment, the ratio of repeating polymer units to lipids in said polymer-conjugated lipid is 50-75. In one embodiment, the number or range is approximately the number or range described hereinabove. In one embodiment, the ratio of repeating polymer units to lipids is the molar ratio.

In one embodiment, the polymer is a polysaccharide, which in one embodiment, is a low molecular weight polysaccharide. In one embodiment, a repeating polymer unit is a repeating to disaccharide unit. In another embodiment, the polymer is not a polysaccharide, which in one embodiment, is Haemaccel.

In one embodiment, the molecular weight of said polysaccharide is between 5 and 20 kD. In one embodiment, the PoS-PL is prepared by reacting a polysaccharide with a phospholipid in a $mass_{PL}$ to $mass_{GAG}$ ratio from about 1:50 to about 1:1, respectively. In another embodiment, said $mass_{PL}$ to $mass_{GAG}$ ratio is from about 1:50 to about 1:10. In another embodiment, said $mass_{PL}$ to $mass_{GAG}$ ratio is from about 1:40 to about 1:1. In another embodiment, said $mass_{PL}$ to $mass_{GAG}$ ratio is from about 1:10 to about 1:40.

In another embodiment, said $mass_{PL}$ to $mass_{GAG}$ ratio is about 1:25. In another embodiment, said $mass_{PL}$ to $mass_{GAG}$ ratio is about 0.5:15. In another embodiment, said $mass_{PL}$ to $mass_{GAG}$ ratio is about 1:15. In another embodiment, said $mass_{PL}$ to $mass_{GAG}$ ratio is about 2:15. In another embodiment, said $mass_{PL}$ to $mass_{GAG}$ ratio is about 5:15.

In another embodiment, the polydispersity of said GAG is from about 1:50 up to 50:50. In another embodiment, the polydispersity of said GAG is from about 1 to 1.75. In another embodiment, the polydispersity of said GAG is from about 1.25 to 1.5.

In one embodiment, the lipid-polymer conjugate of the present invention comprises a low molecular weight polysaccharide wherein the average molecular weight of said polysaccharide is between 5 kD and 90 kd. In another embodiment, the average molecular weight of said polysaccharide is between 5 kD and 60 kD. In another embodiment, the average molecular weight of said polysaccharide is between 5 kD and 40 kD. In another embodiment, the average molecular weight of said polysaccharide is between 5 kD and 15 kD. In another embodiment, the average molecular weight of said polysaccharide is between 5 kD and 20 kD.

In another embodiment, the average molecular weight of said polysaccharide is between 10 kD and 30 kD. In another embodiment, the average molecular weight of said polysaccharide is between 10 kD and 50 kD. In another embodiment, the average molecular weight of said polysaccharide is greater than 10 kD.

In one embodiment, the polysaccharide is a glycosaminoglycan (GAG). In one embodiment, the polymer-conjugated lipid is a glycosaminoglycan-conjugated phospholipid. In one embodiment, a glycosaminoglycan is a mucopolysaccharide. In one embodiment, a glycosaminoglycan is a long chain composed of repeating disaccharide units (aminosugar-acidic sugar repeating units). In one embodiment, the amino sugar is glucosamine or galactosamine. In one embodiment, the amino sugar is sulfated. In one embodiment, the acidic sugar is D-glucuronic acid or L-iduronic acid.

In one embodiment, a glycosaminoglycan encompasses salts and free acids of glycosaminoglycan as well as glycosaminoglycans that have been chemically altered, yet retain their function. These modifications comprise esterification, sulfation, polysulfation, and methylation. For example, hyaluronate salts comprise sodium hyaluronate, potassium hyaluronate, magnesium hyaluronate, and calcium hyaluronate.

In one embodiment, a glycosaminoglycan may be chemically modified to contain more sulfur groups than in their initially extracted form. In another embodiment, a glycosaminoglycan may be partially or completely synthesized and may be of either plant or animal origin.

In one embodiment, glycosaminoglycans are obtained from natural sources. In one embodiment, natural sources of glycosaminoglycans include both plant and animal sources, i.e., beechwood trees and forms of animal cartilage, including shark cartilage, bovine trachea, whale septum, porcine nostrils, and mollusks such as *Perna canaliculus* and sea cucumber. In another embodiment, glycosaminoglycans for use in the present invention are recombinant glycosaminoglycans.

In one embodiment, glycosaminoglycans are then truncated to approximately 10-30 kD for use in the compositions and methods of the present invention.

In one embodiment of the invention, the glycosaminoglycan may be, inter alia, hyaluronic acid, heparin, heparan sulfate, chondrotin sulfate, keratin, keratan sulfate, dermatan sulfate, or a derivative thereof.

In one embodiment, the GAG is hyaluronic acid. In one embodiment, the hyaluronic acid is low molecular weight hyaluronic acid, truncated hyaluronic acid, or a combination thereof. In one embodiment, the low molecular weight hyaluronic acid has an average molecular weight of approximately 10-50 kD.

In one embodiment, polymers of the present invention bind covalently to lipids of the present invention. In one embodiment, high molecular weight GAGs, such as hyaluronic acid with a molecular weight greater than 100 kD, are not used in preparing the liposomes of the present invention, because they were found to adhere non-covalently to the liposomes.

In one embodiment, a low molecular weight GAG, such as sodium hyaluronate is prepared by acid hydrolysis of sodium hyaluronate as described in Example 9 of WO 2010/132402, which is incorporated herein by reference in its entirety.

In one embodiment the molecular weight of hyaluronic acid and derivatives is determined by size exclusion chromatography and multi-angle light scattering (SEC-MALS) as described in WO 2010/132402.

In one embodiment, the polysaccharide is not a glycosaminoglycan (GAG). In one embodiment, the polysaccharide is chitosan, alginic acid, hetastarch, dextran, or a combination thereof.

In one embodiment, a lipid or phospholipid may be used for the compositions and methods of the present invention. In one embodiment, "lipid" refers to any type of lipids including, inter alia, phospholipids, glycerolipids, sphingolipids, sterol lipids, prenol lipids, saccharolipids and the like.

In one embodiment, the polymer-conjugated lipid is a polymer-conjugated phospholipid. In another embodiment, the phospholipid is a phosphatidylethanolamine, a phosphatidylserine, a phosphatidylcholine, a phosphatidylinositol, a phosphatidic acid or a phosphatidylglycerol. In another embodiment, said phospholipid comprises the residue of palmitic acid, myristic acid, myristoleic acid, palmitoleic acid, oleic acid, linoleic acid, linolenic acid, arachidonic acid, eicosapentaenoic acid, erucic acid or docosahexaenoic acid.

In one embodiment, phospholipids for the compositions and methods of the present invention may have varying chain lengths. In one embodiment, said phospholipid is a dimyristoyl phospholipid. In another embodiment, said phospholipid is a dipalmitoyl phospholipid. In another embodiment, said phospholipid is a dilauryl-phospholipid. In another embodiment, said phospholipid is a distearoyl-phospholipid. In another embodiment, said phospholipid is a dioleoyl-phospholipid.

In one embodiment, the present invention provides a liposome comprising a lipid-polymer conjugate represented by the structure of the general formula (A):

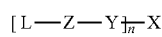
(A)

wherein
L is a lipid or a phospholipid;
Z is either nothing, ethanolamine, serine, inositol, choline, phosphate, or glycerol;
Y is either nothing or a spacer group ranging in length from 2 to 30 atoms;
X is a glycosaminoglycan; and
n is a number from 1 to 70;
wherein any bond between L, Z, Y and X is either an amide or an esteric bond;
wherein the molecular weight of said glycosaminoglycan is between 5 kD and 20 kD.

In one embodiment L is a lipid. In another embodiment L is a phospholipid. In another embodiment, L is a phosphatidylethanolamine, a phosphatidylserine, a phosphatidylcholine, a phosphatidylinositol, a phosphatidic acid or a phosphatidylglycerol. In another embodiment, L comprises the residue of palmitic acid, myristic acid, myristoleic acid, palmitoleic acid, oleic acid, linoleic acid, linolenic acid, arachidonic acid, eicosapentaenoic acid, erucic acid or docosahexaenoic acid. In another embodiment, L is dimyristoyl phosphatidylethanolamine. In another embodiment, said L is dipalmitoyl phosphatidylethanolamine.

In another embodiment, X is hyaluronic acid, heparin, heparan sulfate, chondroitin, chondroitin sulfate, dermatan sulfate or keratan sulfate. In another embodiment, X is hyaluronic acid. In another embodiment, X is heparin. In another embodiment, X is chondroitin. In another embodiment, X is chondroitin sulfate. In another embodiment, X is dermatan sulfate, in another embodiment, X is keratan sulfate. In another embodiment, X is Haemaccel, Alginates, Alginic Acid, Chitosan, or a combination thereof.

In another embodiment, said chondroitin sulfate is chondroitin-6-sulfate, chondroitin-4-sulfate or a derivative thereof. In another embodiment, said dermatan sulfate is dermatan-6-sulfate, dermatan-4-sulfate or a derivative thereof.

In one embodiment, X is a polymer that is not a polysaccharide, which in one embodiment, is Haemaccel. In one embodiment, X is not PEG.

In another embodiment, the present invention provides a liposome comprising a lipid-polymer conjugate represented by the structure of the general formula (I):

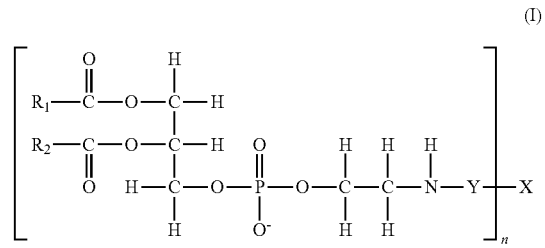

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms; and
X is either a physiologically acceptable monomer, dimer, oligomer or a physiologically acceptable polymer; and
n is a number from 1 to 1,000;
wherein if Y is nothing the phosphatidylethanolamine is directly linked to X via an amide bond and if Y is a spacer, the spacer is directly linked to X via an amide or an esteric bond and to the phosphatidylethanolamine via an amide bond.

In one embodiment, compounds for use in the liposomes of the invention comprise one of the following as the conjugated moiety X: acetate, butyrate, glutarate, succinate, dodecanoate, didodecanoate, maltose, lactobionic acid, dextran, alginate, aspirin, cholate, cholesterylhemisuccinate, carboxymethyl-cellulose, heparin, hyaluronic acid, chondroitin sulfate, polygeline (haemaccel), polyethyleneglycol, polycarboxylated polyethylene glycol, a glycosaminoglycan, a polysaccharide, a hetero-polysaccharide, a homo-polysaccharide, or a polypyranose. The polymers used as starting material to prepare the PE-conjugates may vary in molecular weight from 1 to 2,000 kDa. In one embodiment, heparin is ultra low molecular weight heparin, which in one embodiment, comprises 5-6 disaccharide units.

Examples of phosphatidylethanolamine (PE) moieties are analogues of the phospholipid in which the chain length of the two fatty acid groups attached to the glycerol backbone of the phospholipid varies from 2-30 carbon atoms length, and in which these fatty acids chains contain saturated and/or unsaturated carbon atoms. In lieu of fatty acid chains, alkyl chains attached directly or via an ether linkage to the glycerol backbone of the phospholipid are included as analogues of PE. In one embodiment, the PE moiety is dipalmitoyl-phosphatidyl-ethanolamine. In another embodiment, the PE moiety is dimyristoyl-phosphatidyl-ethanolamine.

Phosphatidyl-ethanolamine and its analogues may be from various sources, including natural, synthetic, and semi-synthetic derivatives and their isomers.

Phospholipids which can be employed in lieu of the PE moiety are N-methyl-PE derivatives and their analogues, linked through the amino group of the N-methyl-PE by a covalent bond; N,N-dimethyl-PE derivatives and their analogues linked through the amino group of the N,N-dimethyl- PE by a covalent bond, phosphatidylserine (PS) and its analogues, such as palmitoyl-stearoyl-PS, natural PS from various sources, semisynthetic PSs, synthetic, natural and artifactual PSs and their isomers. Other phospholipids useful as conjugated moieties in this invention are phosphatidylcholine (PC), phosphatidylinositol (PI), phosphatidic acid and phosphoatidylglycerol (PG), as well as derivatives thereof comprising either phospholipids, lysophospholipids, phosphatidic acid, sphingomyelins, lysosphingomyelins, ceramide, and sphingosine.

For PE-conjugates and PS-conjugates, the phospholipid is linked to the conjugated monomer or polymer moiety through the nitrogen atom of the phospholipid polar head group, either directly or via a spacer group. For PC, PI, and PG conjugates, the phospholipid is linked to the conjugated monomer or polymer moiety through either the nitrogen or one of the oxygen atoms of the polar head group, either directly or via a spacer group.

In another embodiment, the present invention provides a liposome comprising a lipid-polymer conjugate represented by the structure of the general formula (II):

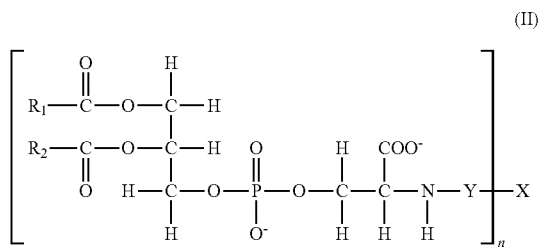

(II)

wherein:
- $R_1$ is a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Y is either nothing or a spacer group ranging in length from 2 to 30 atoms;
- X is a physiologically acceptable monomer, dimer, oligomer or polymer wherein X is a glycosaminoglycan; and
- n is a number from 1 to 1000;
- wherein if Y is nothing, the phosphatidylserine is directly linked to X via an amide bond and if Y is a spacer, the spacer is directly linked to X via an amide or an esteric bond and to the phosphatidylserine via an amide bond.

In one embodiment, the phosphatidylserine may be bonded to Y. or to X if Y is nothing, via the COO$^-$ moiety of the phosphatidylserine.

In another embodiment, the present invention provides a liposome comprising a lipid-polymer conjugate represented by the structure of the general formula (III):

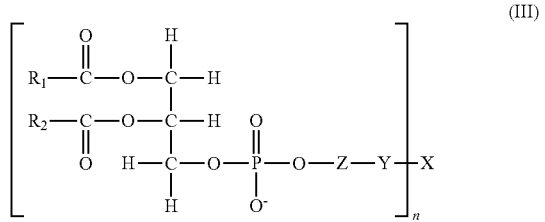

(III)

wherein
- $R_1$ is a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, inositol, choline, or glycerol;
- Y is either nothing or a spacer group ranging in length from 2 to 30 atoms;
- X is a physiologically acceptable monomer, dimer, oligomer, or polymer wherein X is a glycosaminoglycan: and
- n is a number from 1 to 1000;
- wherein any bond between the phosphatidyl, Z, Y and X is either an amide or an esteric bond.

In another embodiment, the present invention provides a liposome comprising a lipid-polymer conjugate represented by the structure of the general formula (IV):

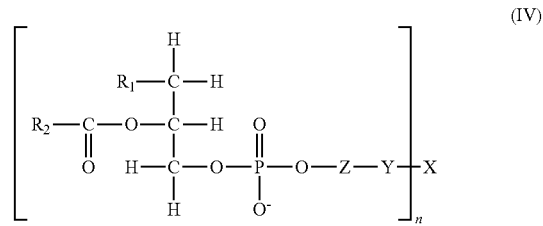

(IV)

wherein
- $R_1$ is either hydrogen or a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, inositol, choline, or glycerol;
- Y is either nothing or a spacer group ranging in length from 2 to 30 atoms;
- X is a physiologically acceptable monomer, dimer, oligomer, or polymer wherein X is a glycosaminoglycan; and
- n is a number from 1 to 1000;
- wherein any bond between the phospholipid, Z, Y and X is either an amide or an esteric bond.

In another embodiment, the present invention provides a liposome comprising a lipid-polymer conjugate represented by the structure of the general formula (V):

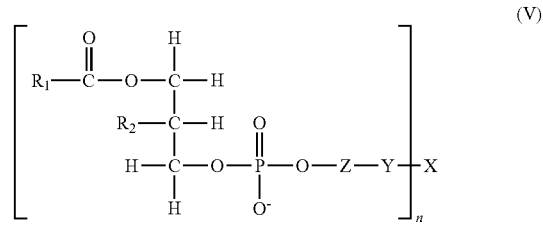

(V)

wherein
- $R_1$ is a linear, saturated, mono-unsaturated, or poly-unsaturated, alkyl chain ranging in length from 2 to 30 carbon atoms;

R₂ is either hydrogen or a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000;

wherein any bond between the phospholipid, Z, Y and X is either an amide or an esteric bond.

In another embodiment, the present invention provides a liposome comprising a lipid-polymer conjugate represented by the structure of the general formula (VI):

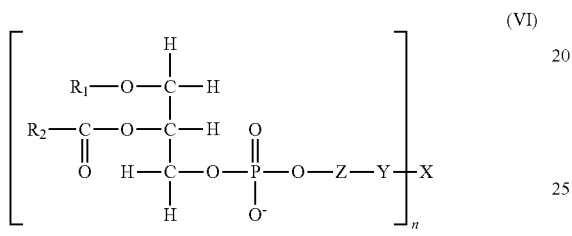

wherein

R₁ is either hydrogen or a linear, saturated, mono-unsaturated, or poly-unsaturated, alkyl chain ranging in length from 2 to 30 carbon atoms;

R₂ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000;

wherein any bond between the phospholipid, Z, Y and X is either an amide or an esteric bond.

In another embodiment, the present invention provides a liposome comprising a lipid-polymer conjugate represented by the structure of the general formula (VII):

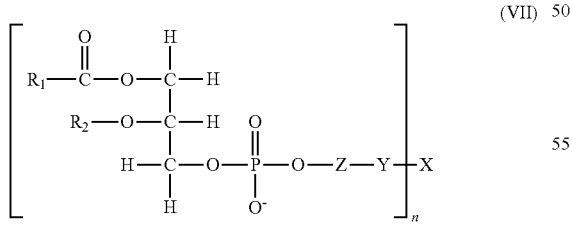

wherein

R₁ is a linear, saturated, mono-unsaturated, or poly-unsaturated, alkyl chain ranging in length from 2 to 30 carbon atoms;

R₂ is either hydrogen or a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000;

wherein any bond between the phospholipid, Z, Y and X is either an amide or an esteric bond.

In one embodiment of the invention, phosphatidylcholine (PC), phosphatidylinositol (PI), phosphatidic acid (PA), wherein Z is nothing, and phosphatidylglycerol (PG) conjugates are herein defined as compounds of the general formula (III).

In another embodiment, the present invention provides a liposome comprising a lipid-polymer conjugate represented by the structure of the general formula (VIII):

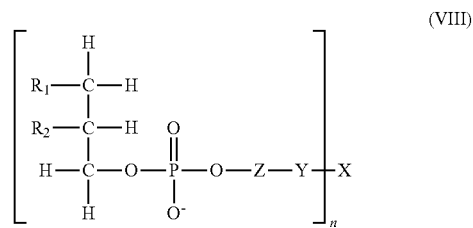

wherein

R₁ is a linear, saturated, mono-unsaturated, or poly-unsaturated, alkyl chain ranging in length from 2 to 30 carbon atoms;

R₂ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000;

wherein any bond between the phospholipid, Z, Y and X is either an amide or an esteric bond.

In another embodiment, the present invention provides a liposome comprising a lipid-polymer conjugate represented by the structure of the general formula (IX):

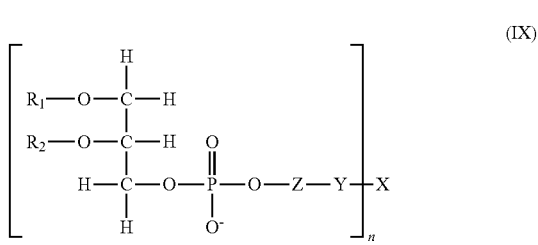

wherein

R₁ is either hydrogen or a linear, saturated, mono-unsaturated, or poly-unsaturated, alkyl chain ranging in length from 2 to 30 carbon atoms;

R₂ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000;

wherein any bond between the phospholipid, Z, Y and X is either an amide or an esteric bond.

In another embodiment, the present invention provides a liposome comprising a lipid-polymer conjugate represented by the structure of the general formula (IXa):

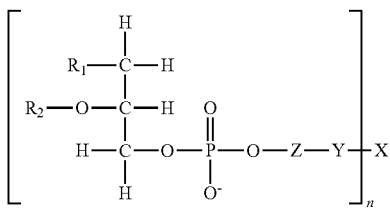

(IXa)

wherein
R₁ is either hydrogen or a linear, saturated, mono-unsaturated, or poly-unsaturated, alkyl chain ranging in length from 2 to 30 carbon atoms;

R₂ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000;

wherein any bond between the phospholipid, Z, Y and X is either an amide or an esteric bond.

In another embodiment, the present invention provides a liposome comprising a lipid-polymer conjugate represented by the structure of the general formula (IXb):

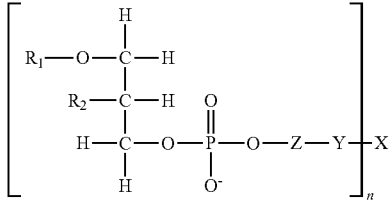

(IXb)

wherein
R₁ is either hydrogen or a linear, saturated, mono-unsaturated, or poly-unsaturated, alkyl chain ranging in length from 2 to 30 carbon atoms;

R₂ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000;

wherein any bond between the phospholipid, Z, Y and X is either an amide or an esteric bond.

In another embodiment, the present invention provides a liposome comprising a lipid-polymer conjugate represented by the structure of the general formula (X):

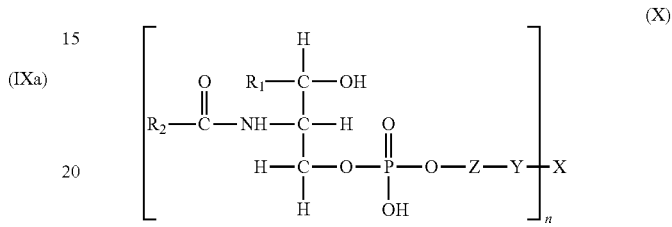

(X)

wherein
R₁ is either hydrogen or a linear, saturated, mono-unsaturated, or poly-unsaturated, alkyl chain ranging in length from 2 to 30 carbon atoms;

R₂ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000;

wherein any bond between the ceramide phosphoryl, Z, Y and X is either an amide or an esteric bond.

In another embodiment, the present invention provides a liposome comprising a lipid-polymer conjugate represented by the structure of the general formula (XI):

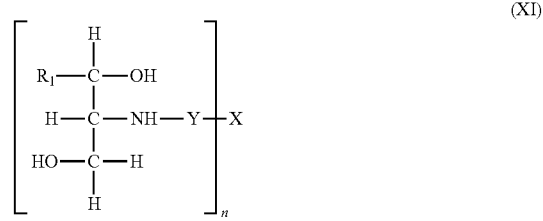

(XI)

wherein
R₁ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a physiologically acceptable monomer, dimer, oligomer or polymer wherein X is a glycosaminoglycan; and n is a number from 1 to 1000;

wherein if Y is nothing the sphingosyl is directly linked to X via an amide bond and if Y is a spacer, the spacer is directly linked to X and to the sphingosyl via an amide bond and to X via an amide or an esteric bond.

In another embodiment, the present invention provides a liposome comprising a lipid-polymer conjugate represented by the structure of the general formula (XII):

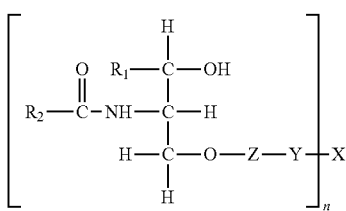

(XII)

wherein
- $R_1$ is a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer or polymer wherein X is a glycosaminoglycan; and
- n is a number from 1 to 1000;
- wherein any bond between the ceramide, Z, Y and X is either an amide or an esteric bond.

In another embodiment, the present invention provides a liposome comprising a lipid-polymer conjugate represented by the structure of the general formula (XIII):

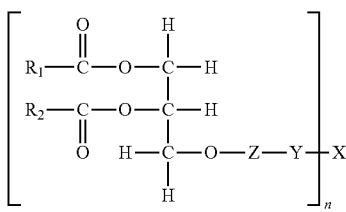

(XIII)

wherein
- $R_1$ is a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein X is a glycosaminoglycan; and
- n is a number from 1 to 1000;
- wherein any bond between the diglyceryl, Z, Y and X is either an amide or an esteric bond.

In another embodiment, the present invention provides a liposome comprising a lipid-polymer conjugate represented by the structure of the general formula (XIV):

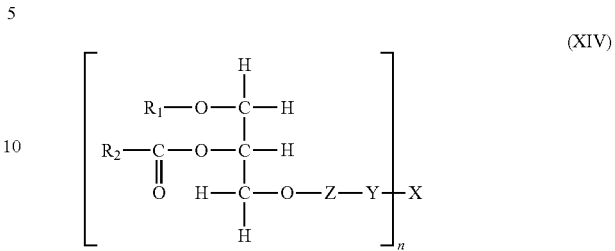

(XIV)

wherein
- $R_1$ is either hydrogen or a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein X is a glycosaminoglycan; and
- n is a number from 1 to 1000;
- wherein any bond between the glycerolipid, Z, Y and X is either an amide or an esteric bond.

In another embodiment, the present invention provides a liposome comprising a lipid-polymer conjugate represented by the structure of the general formula (XV):

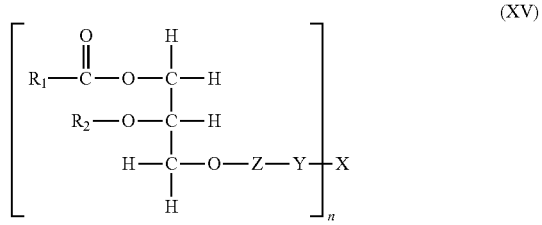

(XV)

wherein
- $R_1$ is a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein X is a glycosaminoglycan; and
- n is a number from 1 to 1000;
- wherein any bond between the glycerolipid, Z, Y and X is either an amide or an esteric bond.

In another embodiment, the present invention provides a liposome comprising a lipid-polymer conjugate represented by the structure of the general formula (XVI):

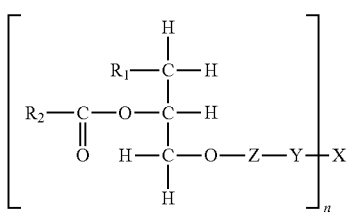

(XVI)

wherein
- $R_1$ is either hydrogen or a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein X is a glycosaminoglycan; and
- n is a number from 1 to 1000;
- wherein any bond between the lipid, Z, Y and X is either an amide or an esteric bond.

In another embodiment, the present invention provides a liposome comprising a lipid-polymer conjugate represented by the structure of the general formula (XVII):

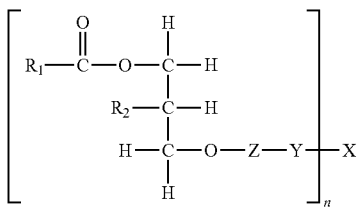

(XVII)

wherein
- $R_1$ is either hydrogen or a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein X is a glycosaminoglycan; and
- n is a number from 1 to 1000;
- wherein any bond between the lipid, Z, Y and X is either an amide or an esteric bond.

In another embodiment, the present invention provides a liposome comprising a lipid-polymer conjugate represented by the structure of the general formula (XVIII):

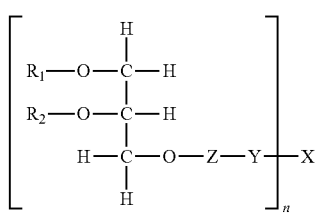

(XVIII)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein X is a glycosaminoglycan; and
- n is a number from 1 to 1000;
- wherein any bond between the lipid, Z, Y and X is either an amide or an esteric bond.

In another embodiment, the present invention provides a liposome comprising a lipid-polymer conjugate represented by the structure of the general formula (XIX):

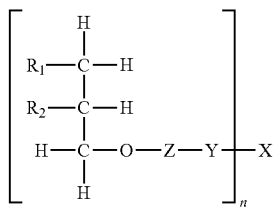

(XIX)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein X is a glycosaminoglycan; and
- n is a number from 1 to 1000;
- wherein any bond between the lipid, Z, Y and X is either an amide or an esteric bond.

In another embodiment, the present invention provides a liposome comprising a lipid-polymer conjugate represented by the structure of the general formula (XX):

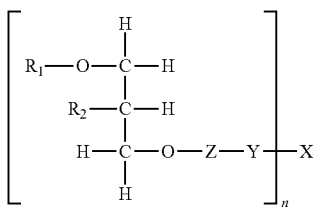

(XX)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein X is a glycosaminoglycan; and
- n is a number from 1 to 1000;
- wherein any bond between the lipid, Z, Y and X is either an amide or an esteric bond.

In another embodiment, the present invention provides a liposome comprising a lipid-polymer conjugate represented by the structure of the general formula (XXI):

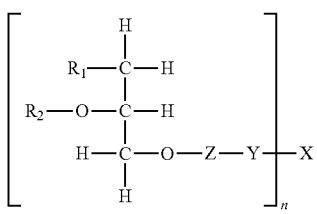

(XXI)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein X is a glycosaminoglycan; and
- n is a number from 1 to 1000;
- wherein any bond between the lipid, Z, Y and X is either an amide or an esteric bond.

For any or all of the compounds represented by the structures of the general formulae (A), (I), (II), (III), (IV), (V), (VI), (VII), (VIII), (IX), (IXa), (IX), (X), (XI), (XII), (XIII), (XIV), (XV), (XVI), (XVII), (XVIII), (XIX), (XX), (XXI), and (XXII) hereinabove: In one embodiment, X is a glycosaminoglycan. According to this aspect and in one embodiment, the glycosaminoglycan may be, inter alia, hyaluronic acid, heparin, heparan sulfate, chondroitin sulfate, keratin, keratan sulfate, dermatan sulfate or a derivative thereof. In another embodiment, X is not a glycosaminoglycan. In another embodiment, X is a polysaccharide, which in one embodiment is a hetero-polysaccharide, and in another embodiment, is a homo-polysaccharide. In another embodiment, X is a polypyranose.

In another embodiment, the glycosaminoglycan is a polymer of disaccharide units. In another embodiment, the number of the disaccharide units in the polymer is m. In another embodiment, m is a number from 2-10,000. In another embodiment, m is a number from 2-500. In another embodiment, m is a number from 2-1000. In another embodiment, m is a number from 50-500. In another embodiment, m is a number from 2-2000. In another embodiment, m is a number from 500-2000. In another embodiment, m is a number from 1000-2000. In another embodiment, m is a number from 2000-5000. In another embodiment, m is a number from 3000-7000. In another embodiment, m is a number from 5000-10,000. In another embodiment, a disaccharide unit of a glycosaminoglycan may be bound to one lipid or phospholipid moiety. In another embodiment, each disaccharide unit of the glycosaminoglycan may be bound to zero or one lipid or phospholipid moieties. In another embodiment, the lipid or phospholipid moieties are bound to the —COOH group of the disaccharide unit. In another embodiment, the bond between the lipid or phospholipid moiety and the disaccharide unit is an amide bond.

In another embodiment, the glycosaminoglycan comprises di- or trisaccharide unit monomers of glycosaminoglycans.

In another embodiment, the chondroitin sulfate may be, inter alia, chondroitin-6-sulfate, chondroitin-4-sulfate or a derivative thereof.

In one embodiment of the invention, Y is nothing. Non-limiting examples of suitable divalent groups forming the optional bridging group (which in one embodiment, is referred to as a spacer) Y, according to embodiments of the invention, are straight or branched chain alkylene, e.g., of 2 or more, preferably 4 to 30 carbon atoms, —CO-alkylene-CO, —NH-alkylene-NH—, —CO-alkylene-NH—, —NH-alkylene-NH—, CO-alkylene-NH—, an amino acid, cycloalkylene, wherein alkylene in each instance, is straight or branched chain and contains 2 or more, preferably 2 to 30 atoms in the chain, —(—O—CH(CH$_3$)CH$_2$—)$_x$— wherein x is an integer of 1 or more.

According to embodiments of the invention, in addition to the traditional phospholipid structure, related derivatives for use in this invention are phospholipids modified at the C1 or C2 position to contain an amine, ether or alkyl bond instead of an ester bond. In one embodiment of the invention, the alkyl phospholipid derivatives and ether phospholipid derivatives are exemplified herein.

In one embodiment of the invention, the sugar rings of the phospholipid-bound glycosaminoglycan are, intact. In another embodiment, intact refers to closed. In another embodiment, intact refers to natural. In another embodiment, intact refers to unbroken.

In one embodiment of the invention, the structure of the lipid or phospholipid in any compound according to the invention is intact. In another embodiment, the natural structure of the lipid or phospholipids in any compound according to the invention is maintained.

In one embodiment, the compounds for use in the present invention are biodegradable.

In some embodiments, the compounds for use are as listed in Table 1 below.

TABLE 1

Sample Polymer-conjugated Lipids.

| Phospholipid | Spacer | Polymer (m.w.) | Compound |
|---|---|---|---|
| PE | None | Hyaluronic acid (2-2000 kDa) | XXII |
| Dimyristoyl-PE | None | Hyaluronic acid | XXIII |
| PE | None | Heparin (0.7-110 kDa) | XXIV |
| PE | None | Chondroitin sulfate A | XXV |
| PE | None | Carboxymethylcellulose (20-500 kDa) | XXVI |
| PE | Dicarboxylic acid + Diamine | Polygeline (haemaccel) (4-100 kDa) | XXVII |
| PE | None | Hydroxyethylstarch | XXVIII |
| PE | Dicarboxylic acid + Diamine | Dextran (1-2,000 kDa) | XXIX |
| PE | None | Aspirin | XXX |
| PE | Carboxyl amino group | Hyaluronic acid (2-2000 kDa) | XXXI |
| PE | Dicarboxyl group | Hyaluronic acid (2-2000 kDa) | XXXII |
| PE | Dipalmitoic acid | Hyaluronic acid (2-2000 kDa) | XXXIII |
| PE | Carboxyl amino group | Heparin (0.5-110 kDa) | XXXIV |
| PE | Dicarboxyl group | Heparin (0.5-110 kDa) | XXXV |
| PE | Carboxyl amino group | Chondroitin sulfate A | XXXVI |
| PE | Dicarboxyl group | Chondroitin sulfate A | XXXVII |
| PE | Carboxyl amino group | Carboxymethylcellulose (20-500 kDa) | XXXVIII |
| PE | Dicarboxyl group | Carboxymethylcellulose (20-500 kDa) | XXXIX |
| PE | None | Polygeline (haemaccel) (4-100 kDa) | XL |
| PE | Carboxyl amino group | Polygeline (haemaccel) (4-40 kDa) | XLI |
| PE | Dicarboxyl group | Polygeline (haemaccel) (4-40 kDa) | XLII |
| PE | Carboxyl amino group | Hydroxyethylstarch | XLIII |
| PE | Dicarboxyl group | Hydroxyethylstarch | XLIV |
| PE | None | Dextran (1-2,000 kDa) | XLV |
| PE | Carboxyl amino group | Dextran (1-2,000 kDa) | XLVI |
| PE | Dicarboxyl group | Dextran (1-2,000 kDa) | XLVII |
| PE | Carboxyl amino group | Aspirin | XLVIII |
| PE | Dicarboxyl group | Aspirin | XLIX |
| PE | None | Albumin | L |
| PE | None | Alginate (2-2000 kDa) | LI |
| PE | None | Polyaminoacid | LII |
| PE | None | Polyethylene glycol | LIII |
| PE | None | Lactobionic acid | LIV |
| PE | None | Acetylsalicylate | LV |
| PE | None | Cholesteryl- hemmisuccinate | LVI |
| PE | None | Maltose | LVII |
| PE | None | Cholic acid | LVIII |
| PE | None | Chondroitin sulfates | LIX |
| PE | None | Polycarboxylated polyethylene glycol | LX |
| Dipalmitoyl-PE | None | Hyaluronic acid | LXI |
| Dipalmitoyl-PE | None | Heparin | LXII |
| Dipalmitoyl-PE | None | Chondroitin sulfate A | LXIII |
| Dipalmitoyl-PE | None | Carboxymethylcellulose | LXIV |
| Dipalmitoyl-PE | None | Polygeline (haemaccel) | LXV |
| Dipalmitoyl-PE | None | Hydroxyethylstarch | LXVI |
| Dipalmitoyl-PE | None | Dextran | LXVII |
| Dipalmitoyl-PE | None | Aspirin | LXVIII |
| Dimyristoyl-PE | None | Heparin | LXVIX |
| Dimyristoyl-PE | None | Chondroitin sulfate A | LXX |
| Dimyristoyl-PE | None | Carboxymethylcellulose | LXXI |
| Dimyristoyl-PE | None | Polygeline (haemaccel) | LXXII |
| Dimyristoyl-PE | None | Hydroxyethylstarch | LXXIII |
| Dimyristoyl-PE | None | Dextran | LXXIV |
| Dimyristoyl-PE | None | Aspirin | LXXV |
| PS | None | Hyaluronic acid | LXXVI |
| PS | None | Heparin | LXXVII |
| PS | None | Polygeline (haemaccel) | LXXVIII |
| PC | None | Hyaluronic acid | LXXIX |

TABLE 1-continued

Sample Polymer-conjugated Lipids.

| Phospholipid | Spacer | Polymer (m.w.) | Compound |
| --- | --- | --- | --- |
| PC | None | Heparin | LXXX |
| PC | None | Polygeline (haemaccel) | LXXXI |
| PI | None | Hyaluronic acid | LXXXII |
| PI | None | Heparin | LXXXIII |
| PI | None | Polygeline (haemaccel) | LXXXIV |
| PG | None | Hyaluronic acid | LXXXV |
| PG | None | Heparin | LXXXVI |
| PG | None | Polygeline (haemaccel) | LXXXVII |
| PE | None | Glutaryl | LXXXVIII |
| PE | Amino Acid | Hyaluronic Acid | LXXXVIX |
| PE | Amino Acid | Chondroitin Sulfate | XC |
| PE | Amino Acid | Dermatan Sulfate | XCI |
| PE | Amino Acid | Heparin | XCII |
| PS | Amino Acid | Hyaluronic Acid | XCIII |
| PS | Amino Acid | Chondroitin Sulfate | XCIV |
| PS | Amino Acid | Dermatan Sulfate | XCV |
| PS | Amino Acid | Heparin | XCVI |
| PC | Amino Acid | Hyaluronic Acid | XCVII |
| PC | Amino Acid | Chondroitin Sulfate | XCVIII |
| PC | Amino Acid | Dermatan Sulfate | XCIX |
| PC | Amino Acid | Heparin | C |
| PE | Amino Acid | Alginate (2-2000 kDa) | CI |
| PE | None | Dermatan Sulfate | CII |
| PS | None | Dermatan Sulfate | CIII |
| PC | None | Dermatan Sulfate | CIV |
| PI | None | Dermatan Sulfate | CV |
| PG | None | Dermatan Sulfate | CVI |
| PE | None | Chitosan | CVII |
| PS | None | Chitosan | CVIII |
| PC | None | Chitosan | CIX |
| PI | None | Chitosan | CX |
| PG | None | Chitosan | CXI |
| PE | Dicarboxylic Acid | Chitosan | CXII |
| PS | Dicarboxylic Acid | Chitosan | CXIII |
| PC | Dicarboxylic Acid | Chitosan | CXIV |
| PI | Dicarboxylic Acid | Chitosan | CXV |
| PG | Dicarboxylic Acid | Chitosan | CXVI |

In one embodiment, a GAG and a PL for use in the compositions and methods of the present invention comprise a spacer, which in one embodiment, is an amino acid, wherein the amino group of the amino acid binds to a carboxy group of the GAG and the carboxy group of the amino acid binds to an amino group of the phospholipids.

In one embodiment of the invention, the compounds for use in the present invention are any one or more of Compounds I-LXXXVIII. In another embodiment, the compounds for use in the present invention are Compound XXII, Compound XXIII, Compound XXIV, Compound XXV, Compound XXVI, Compound XXVII, Compound XXVIII, Compound XXIX, Compound XXX, or pharmaceutically acceptable salts thereof, in combination with a physiologically acceptable carrier or solvent. According to embodiments of the invention, these polymers, when chosen as the conjugated moiety, may vary in molecular weights from 200 to 2,000,000 Daltons. In one embodiment of the invention, the molecular weight of the polymer as referred to herein is from 200 to 1000 Daltons. In another embodiment, the molecular weight of the polymer as referred to herein is from 200 to 1000 Daltons. In another embodiment, the molecular weight of the polymer as referred to herein is from 1000 to 5000 Daltons. In another embodiment, the molecular weight of the polymer as referred to herein is from 5000 to 10,000 Daltons. In another embodiment, the molecular weight of the polymer as referred to herein is from 10,000 to 20,000 Daltons. In another embodiment, the molecular weight of the polymer as referred to herein is from 10,000 to 50,000 Daltons. In another embodiment, the molecular weight of the polymer as referred to herein is from 20,000 to 70,000 Daltons. In another embodiment, the molecular weight of the polymer as referred to herein is from 50,000 to 100,000 Daltons. In another embodiment, the molecular weight of the polymer as referred to herein is from 100,000 to 200,000 Daltons. In another embodiment, the molecular weight of the polymer as referred to herein is from 200,000 to 500,000 Daltons. In another embodiment, the molecular weight of the polymer as referred to herein is from 200,000 to 1,000,000 Daltons. In another embodiment, the molecular weight of the polymer as referred to herein is from 500,000 to 1,000,000 Daltons. In another embodiment, the molecular weight of the polymer as referred to herein is from 1,000,000 to 2,000,000 Daltons. Various molecular weight species have been shown to have the desired biological efficacy.

In one embodiment of this invention, low molecular weight Lipid-conjugates are defined hereinabove as the compounds of formula (I)-(XXI) wherein X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, hyaluronic acid, glycosaminoglycan, or polypyranose.

Examples of suitable divalent groups forming the optional bridging group Y are straight- or branched-chain alkylene, e.g., of 2 or more, preferably 4 to 18 carbon atoms, —CO—alkylene-CO, —NH-alkylene-NH—, —CO-alkylene-NH—, cycloalkylene, wherein alkylene in each instance, is straight or branched chain and contains 2 or mom, preferably 2 to 18 carbon atoms in the chain, —(—O—CH(CH$_3$)CH$_2$—)$_x$— wherein x is an integer of 1 or more.

In another embodiment, in addition to the traditional phospholipid structure, related derivatives for use in this invention are phospholipids modified at the C1 or C2 position to contain an ether or alkyl bond instead of an ester bond. These derivatives are exemplified hereinabove by the general formulae (VIII) and (IX).

In one embodiment of the invention, X is covalently conjugated to a lipid. In another embodiment, X is covalently conjugated to a lipid via an amide bond. In another embodiment, X is covalently conjugated to a lipid via an esteric bond. In another embodiment, the lipid is phosphatidylethanolamine.

In one embodiment, the present invention provides a liposome comprising a polymer-conjugated lipid, which in one embodiment, is a polysaccharide-conjugated phospholipid (PoS-PL). In one embodiment, said PoS-PL is hyaluronic acid-phosphatidyl-ethanolamine (HyPE; Compound A), which in one embodiment, comprises alternating N-acetyl-D-glucosamine and D-glucuronic acid residues joined by alternating beta-1,3-glucuronidic and beta-1,4-glucosaminidic bonds.

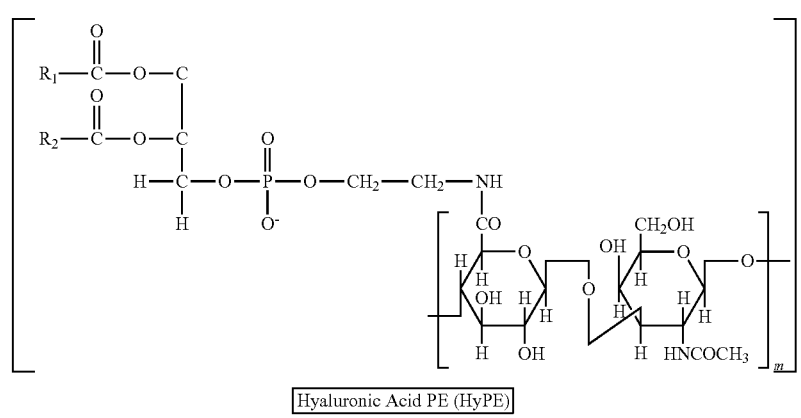

Compound A

Hyaluronic Acid PE (HyPE)

In one embodiment derivatives of hyaluronic acid such as those obtained from chemical modification by salification, partial and/or total esterification, inner esterification, deacetylation, O-sulphatation, percarboxylation and amidation may be used in the compositions and methods of the present invention. In one embodiment, "n" describes the number of PEs present in the whole HyPE-conjugated PE molecule, while "m" describes the number of disaccharides present in the molecule, wherein some of the disaccharide units comprise a conjugated HyPE, and other disaccharide units do not comprise a conjugated HyPE.

In another embodiment, said PoS-PL is Chondroitin Sulfate-phosphatidyl-ethanolamine (CSAPE; Compound B).

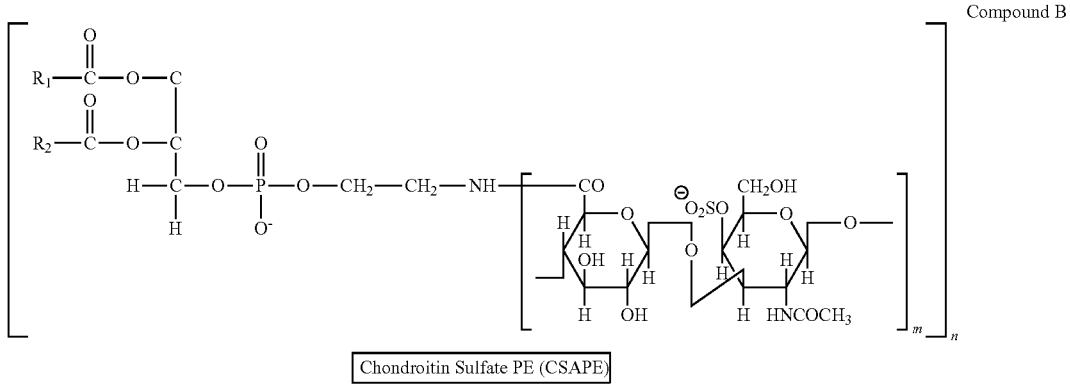

Compound B

Chondroitin Sulfate PE (CSAPE)

In another embodiment, said PoS-PL is Dermatan Sulfate-phosphatidyl-ethanolamine (DerPE: Compound C).

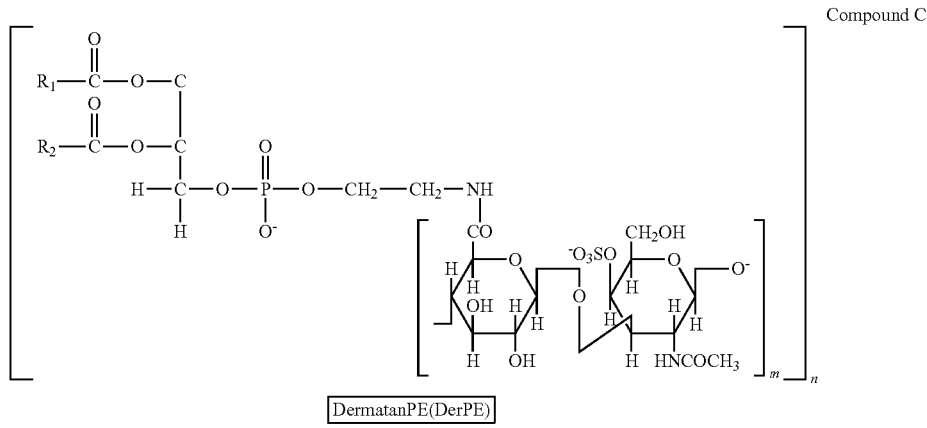

Compound C

DermatanPE(DerPE)

In another embodiment, said PoS-PL is Heparin-phosphatidyl-ethanolamine (HepPE; Compound D).

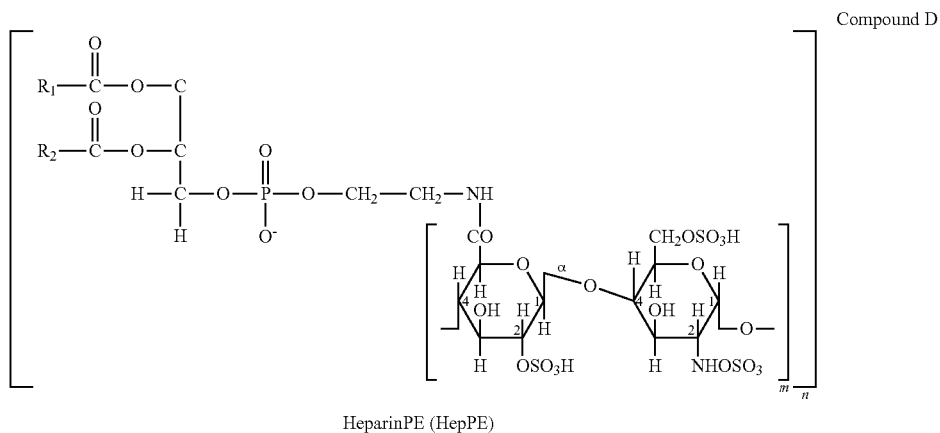

Compound D

HeparinPE (HepPE)

In another embodiment, said PoS-PL is a non-glycosaminoglycan-conjugated phospholipid.

In another embodiment, said PoS-PL is Chitosan-Glutaryl-phosphatidyl-ethanolamine (ChiPE; Compound E).

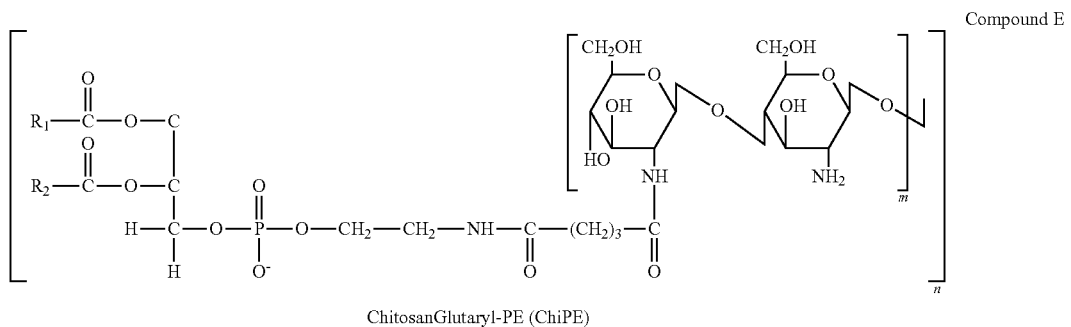

Compound E

ChitosanGlutaryl-PE (ChiPE)

In another embodiment, said PoS-PL is Alginic acid-phosphatidyl-ethanolamine Compound F).

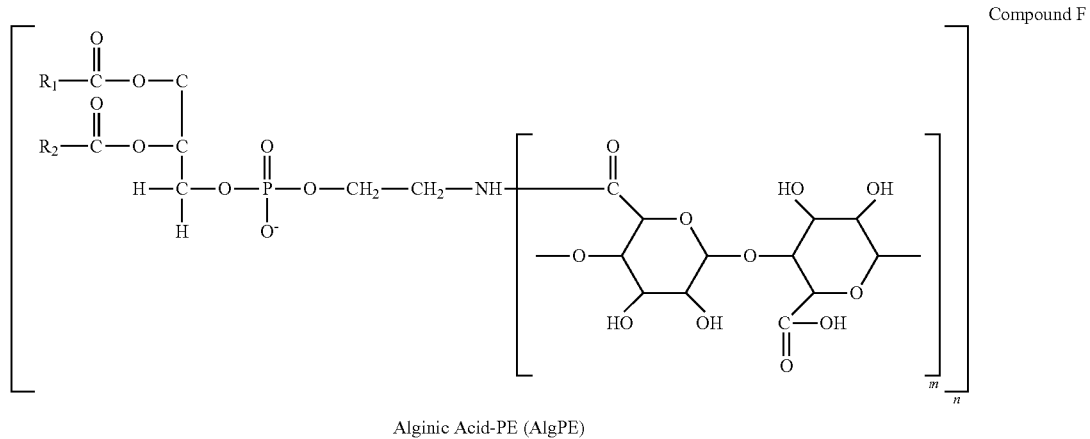

Alginic Acid-PE (AlgPE)

In another embodiment, said PoS-PL is Hetastarch-Glutaryl-phosphatidyl-ethanolamine (HetPE; Compound G).

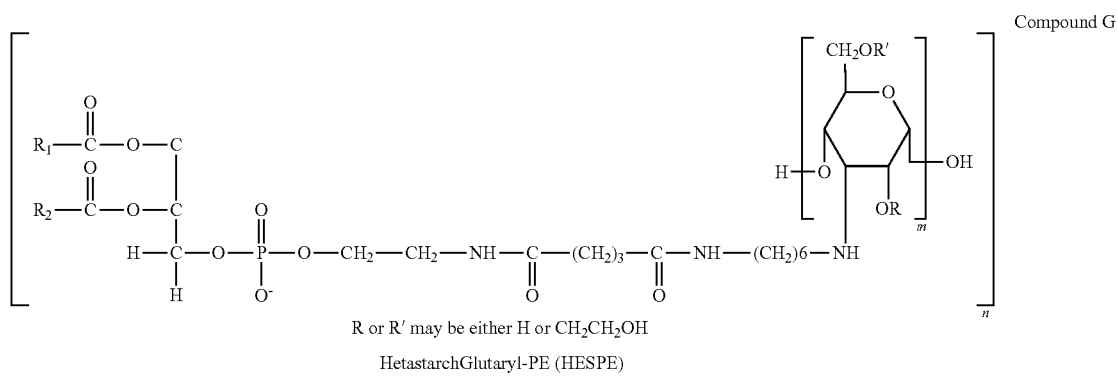

R or R' may be either H or $CH_2CH_2OH$

HetastarchGlutaryl-PE (HESPE)

In another embodiment, said PoS-PL is Dextran-Glutaryl-phosphatidyl-ethanolamine (DexPE; Compound H).

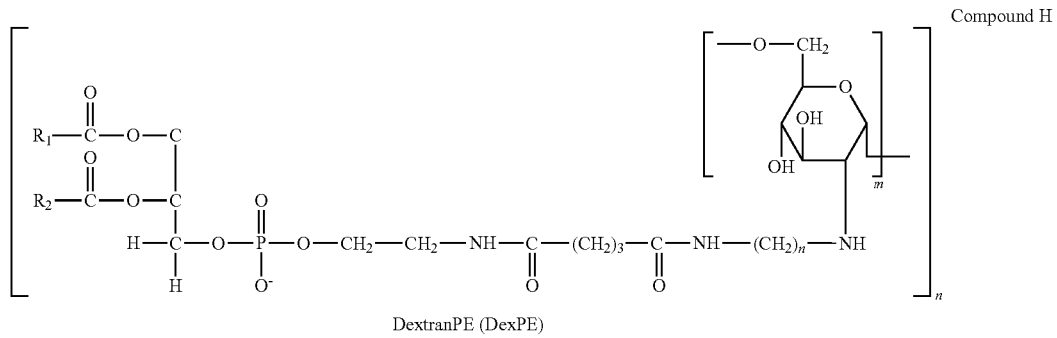

DextranPE (DexPE)

In another embodiment, said Po-L is Haemaccel-Glutaryl-phosphatidyl-ethanolamine (HemPE or polygeline; Compound 1).

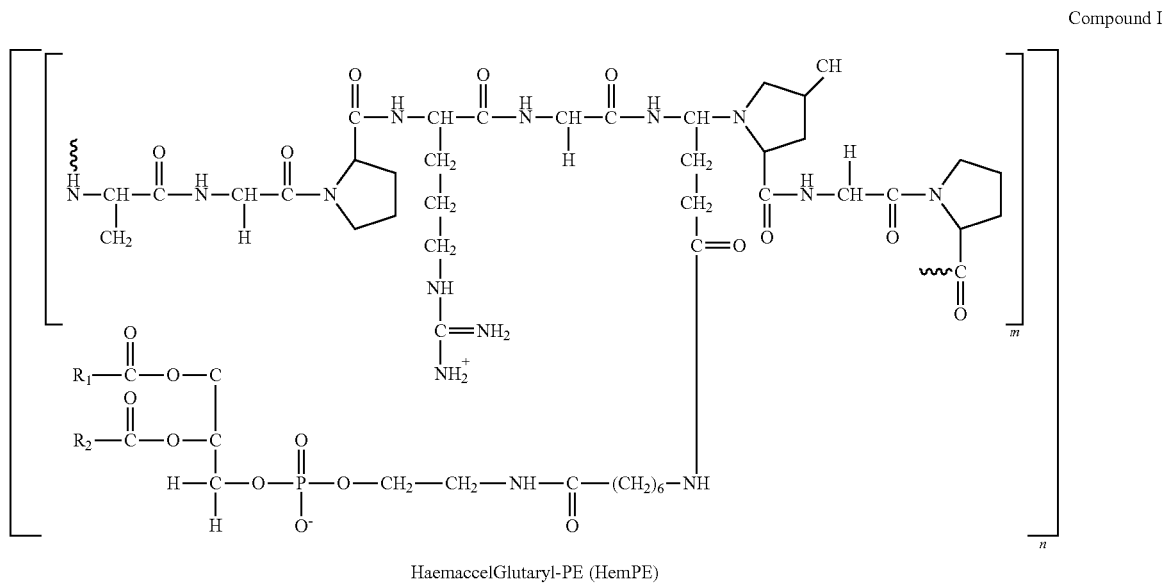

HaemaccelGlutaryl-PE (HemPE)

In one embodiment, said PoS-PL is keratan sulfate-phosphatidyl-ethanolamine (KSPE; Compound J).

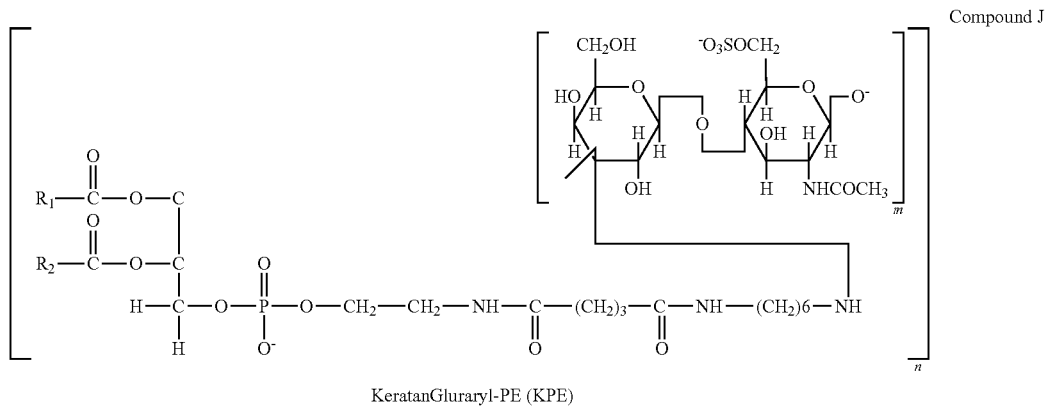

KeratanGluraryl-PE (KPE)

In another embodiment, said PoS-PL is a lipid or phospholipid conjugate as described in US Publication No. US2010/0022473, which is incorporated herein by reference.

In one embodiment, a polysaccharide is linked to a phospholipid through an amine residue of the phospholipid. In one embodiment, a polysaccharide is linked to a phospholipid through a carboxylic acid residue of the polysaccharide. In another embodiment, a polysaccharide is linked to a phospholipid via a hydroxyl units (e.g., —$CH_2$—OH), which may be oxidized to an aldehyde in the absence of a crosslinking reagent.

In one embodiment, liposomes are hollow microspheres of varying size, ranging between 50 nm and 1000 nm, formed by one or more double lipid layers that enclose a hydrophilic core. This structure can be achieved thanks to the special nature of phospholipids that have a hydrophobic tail and hydrophilic head; in an aqueous medium the hydrophobic tails attract one another while the hydrophilic heads tend to face water. The result is double lipid layers that close to form small vesicles inside which them is a variously hydrophilic environment. Liposomes were first described in 1965 (Standish M M et al., J Mol Biol, 1965, 13:238-252) and have been researched as carriers for drugs and/or active ingredients (e.g., Liposomes as drug carriers, Gregoriadis G. editor, New York: John Wiley & Sons, 1985: 3-18; Banerjee R., J Biomater Appl, 2001, 16:3-21). They are normally classified on the basis of their size and the number of double lipid layers. Generally speaking, as described, for example, by Callow R A et al. (Cryobiology, 1985:251-267, incorporated herein by reference), reference is made to a) multilamellar vesicles: they have an onion-like structure wherein a number of double lipid layers are interspersed with hydrophilic layers; b) unilamellar vesicles, large (diameter of over 1 .mu.m) and small (diameter of less than 1 .mu.m): they are formed by one single double lipid layer and enclose a strongly hydrophilic nucleus; c) oligolamellar vesicles, constituted by several double lipid layers that enclose a markedly hydrophobic environment.

In one embodiment, liposomes, which in one embodiment are, multilamellar vesicles (MLV), microemulsified liposomes (MEL) or large unilamellar vesicles (LUVET), are prepared using methods known in the art. In one embodiment, said liposomes do not comprise phosphatidylethanolamine (PE). In another embodiment, said liposomes comprise phosphatidylethanolamine.

In one embodiment, the classic lipid film technique for the production of unilamellar liposomes was used to prepare liposomes: the lipids selected that will constitute the double layer are mixed with an organic solvent and then exposed to set environmental conditions (for example, set parameters of pressure and temperature) so as to allow the solvent to evaporate and the dry lipid film to form. The lipid film is then hydrated with an aqueous medium and/or with the solution containing the polymer to be associated with the liposomes. One part of the mixture is frozen, freeze-dried and then reconstituted to its initial volume by adding a suitable medium. The step of freezing, freeze-drying and reconstituting was devised on the basis of experimental findings (Peer at al., Biochim Biophys Acta, 2003, 1612: 76-82, incorporated herein by reference) demonstrating that hyaluronic acid and/or the derivatives thereof can act as cryoprotectors for the unilamellar liposome microstructures. Generally, when simple, structured-phospholipid suspensions are freeze-dried and then reconstituted, the liposomes lose their original characteristics, and become organized in far larger multilamellar vesicles, that are unsuitable for the purposes of the present invention because their structure and the controlled release of the material they are carrying arm ineffective. The presence in the mixture to be freeze-dried of significant quantities of polysaccharides conserves the original structural properties of the liposomes by the formation of stabilizing hydrogen bonds and maintains their efficacy as controlled release systems following their reconstitution.

In another embodiment, liposomes of the present invention may be obtained by any method known to the skilled artisan. In one embodiment, liposomes of appropriate size are prepared using sonication/ultrasound, extrusion, or a combination thereof.

In another embodiment, the liposome preparation can be produced by reverse phase evaporation (REV) method (see U.S. Pat. No. 4,235,871, incorporated herein by reference), infusion procedures, or detergent dilution. A review of these and other methods for producing liposomes may be found in the text Liposomes, Marx Ostro, ed., Marcel Dekker, Inc., New York, 1983, Chapter 1, incorporated herein by reference. See also Szoka Jr. et al., (1980. Ann. Rev. Biophys. Bioeng., 9:467), incorporated herein by reference. A method for forming ULVs is described in Cullis et al., PCT Publication No. 87/00238, Jan. 16, 1986, entitled "Extrusion Technique for Producing Unilamellar Vesicles", incorporated herein by reference. Multilamellar liposomes (MLV) may be prepared by the lipid-film method, wherein the lipids are dissolved in a chloroform-methanol solution (3:1, vol/vol), evaporated to dryness under reduced pressure and hydrated by a swelling solution. Then, the solution is subjected to extensive agitation and incubation, e.g., 2 hour, e.g., at 37.degree. C. After incubation, unilamellar liposomes (ULV) are obtained by extrusion. The extrusion step modifies liposomes by reducing the size of the liposomes to a preferred average diameter. Alternatively, liposomes of the desired size may be selected using techniques such as filtration or other size selection techniques.

While the size-selected liposomes of the invention should have an average diameter of less than about 300 nm, it is preferred that they are selected to have an average diameter of less than about 200 nm with an average diameter of less than about 100 nm being particularly preferred. When the liposome of the present invention is a unilamellar liposome, it preferably is selected to have an average diameter of less than about 200 nm. The most preferred unilamellar liposomes of the invention have an average diameter of less than about 100 nm. It is understood, however, that multivesicular liposomes of the invention derived from smaller unilamellar liposomes will generally be larger and may have an average diameter of about less than 100) nm. Preferred multivesicular liposomes of the invention have an average diameter of less than about 800 nm, and less than about 500 nm while most preferred multivesicular liposomes of the invention have an average diameter of less than about 300 nm.

In one embodiment, the liposomes are formed by a lipid constituted by a hydrophilic part and a lipophilic part that may have a single or multiple, saturated or unsaturated, linear or branched chain, of natural or synthetic origin. Other elements may be added, such as cholesterol, which stabilize the liposomes in the biological fluids, or any other element known to the expert in the field to have the desired effect.

In one embodiment, a liposome of the present invention comprises two or more lateral lipophilic chains. In one embodiment, a liposome of the present invention comprises the lipophilic cationic chains that contain two saturated and/or unsaturated fatty acids with, for example, between 10 and 30 carbon atoms, the salts of fatty acids with quaternary amines, quaternary dimethyldiacylamines where the acyl groups contain between 8 and 30 carbon atoms. Further examples are amply described in the literature (including Fasbender et al., Am J Physiol, 1995, 269:L45-L51; Solodin et al, Biochemistry, 1995, 34:13537-13544; Felgner et al., J Biol Chem, 1994, 269:2550-2561; Stamatatos et al., Biochemistry, 1988, 27:3917-3925, incorporated herein by reference in their entirety).

In one embodiment, a liposome of the present invention comprises non-ionic chains, which in one embodiment are glyceric diesters with, for example, between 10 and 30 carbon atoms, and in another embodiment, are alkoxylated amines. In one embodiment, examples of anionic lateral chains including phosphatidic acids and negatively charged phospholipids such as dipalmitoylphosphatidylglycerol. In one embodiment, examples of substances with a single, non-ionic chain are monoglyceric esters with between 10 and 30 carbon atoms in the chain, such as glyceryl caprate, caprylate, hydroxystearate, lysostearate, lanolate, laurate, linolate, etc.

In another embodiment, liposomes are constituted by polyoxyethylene derivatives to which lipophilic chains are bound by ether and/or ester bonds. For illustrative purposes we can mention cetyl and stearic ethers, and all those with between 3 and 10 oxyethylene units, and the derivatives thereof.

The substances with a single anionic chain include, but are not limited to, fatty acids such as oleic acid and negatively charged phospholipids with a single chain such as phosphatidylserine and phosphatidylglycerol.

In one embodiment, the liposome may be constituted by phospholipids of either natural or synthetic origin. Natural phospholipids include egg phosphatidylcholine, as such or hydrogenated, and phospholipids from soya or other vegetal sources.

Liposomes according to the invention may be produced from combinations of lipid materials well known and routinely utilized in the art to produce liposomes. Lipids may include relatively rigid varieties, such as sphingomyelin, or fluid types, such as phospholipids having unsaturated acyl chains. "Phospholipid" refers to any one phospholipid or combination of phospholipids capable of forming liposomes. Phosphatidylcholines (PC), including those obtained from egg, soy beans or other plant sources or those that are partially or wholly synthetic, or of variable lipid chain length and unsaturation are suitable for use in the present invention. Synthetic, semisynthetic and natural product phosphatidylcholines including, but not limited to, distearoylphosphatidylcholine (DSPC), hydrogenated soy phosphatidylcholine (HSPC), soy phosphatidylcholine (soy PC), egg phosphatidylcholine (egg PC), hydrogenated egg phosphatidylcholine (HEPC), dipalmitoylphosphatidylcholine (DPPC), dimyristoylphosphatidylcholine (DMPC) dimiristoylglycerophosphocholine (DMPC), dilauroylglycerophosphocholine (DLPC), palmitoyloleoylglycerophospho-choline (POPC), phosphatidylethanolamine, dipalmitoylphosphatidylglycerol (DPPG), dipalmitoylphosphatidic acid (DPPA), and phosphatidylserine are suitable phosphatidylcholines for use in this invention. All of these phospholipids are commercially available. Further, phosphatidylglycerols (PG) and phosphatic acid (PA) are also suitable phospholipids for use in the present invention and include, but are not limited to, dimyristoylphosphatidylglycerol (DMPG), dilaurylphosphatidylglycerol (DLPG), dipalmitoylphosphatidylglycerol (DPPG), distearoylphosphatidylglycerol (DSPG) dimyristoylphosphatidic acid (DMPA), distearoylphosphatidic acid (DSPA), dilaurylphosphatidic acid (DLPA), and dipalmitoylphosphatidic acid (DPPA). In another embodiment, liposomes are composed of di-oleoyl-phosphatidyl-choline (DOPC), PC labeled with $C_6$-NBD (a fluorescent fatty acid) at carbon 2, or a combination thereof. In another embodiment, liposomes are composed of dimyristoyl phosphatidylcholine (DMPC). Other suitable phospholipids include phosphatidylethanolamines, phosphatidylinositols, sphingomyelins, and phosphatidic acids containing lauric, myristic, stearoyl, and palmitic acid chains. For the purpose of stabilizing the lipid membrane, it is preferred to add an additional lipid component, such as cholesterol. In one embodiment, lipids for producing liposomes according to the invention include phosphatidylethanolamine (PE) and phosphatidylcholine (IV) in further combination with cholesterol (CH). According to one embodiment of the invention, a combination of lipids and cholesterol for producing the liposomes of the invention comprise a PE:PC:Chol molar ratio of 3:1:1.

In one embodiment, in order to prevent the uptake of the liposomes into the cellular endothelial systems and enhance the uptake of the liposomes into the tissue of interest, the outer surface of the liposomes may be modified with a long-circulating agent. The modification of the liposomes with a hydrophilic polymer as the long-circulating agent is known to enable to prolong the half-life of the liposomes in the blood. Examples of the hydrophilic polymer include polyethylene glycol, polymethylethylene glycol, polyhydroxypropylene glycol, polypropylene glycol, polymethylpropylene glycol and polyhydroxypropylene oxide. Thus, in one embodiment, incorporation of polyethylene glycol (PEG) containing phospholipids is also contemplated by the present invention.

Clearly, there are a multitude of possible combinations that can be made to obtain liposomes that are suitable for the purpose and, since they have already been amply reported in the literature, a technical expert in the field will be able to choose the most suitable.

In one embodiment, the compounds according to the invention are biodegradable.

Methods of Producing Polymer-Conjugated Lipid Liposomes

In another embodiment, the present invention provides a method of producing a mixed liposome comprising the step of conjugating a lipid with a polymer to form a polymer-conjugated lipid and contacting said polymer-conjugated lipid with a liposome to produce a mixed liposome.

In another embodiment, the present invention provides a method of producing a modified liposome comprising the step of conjugating a lipid with a polymer to form a polymer-conjugated lipid and contacting said polymer-conjugated lipid with a liposome to produce a modified liposome. In one embodiment, the method further comprises the step of isolating said polymer-conjugated lipid prior to the step of contacting the PoS-PL with the liposome. In one embodiment, the liposome comprises two or more polymer-conjugated lipids.

In another embodiment, the present invention provides a mixed liposome produced by the method comprising the step of conjugating a lipid with a polymer to form a polymer-conjugated lipid and contacting said polymer-conjugated lipid with a liposome to produce a mixed liposome.

Methods of Producing Liposomes

In one embodiment, liposomes are prepared by providing phospholipids in an aqueous environment and allowing said phospholipids to form liposomes. In one embodiment, energy is supplied to speed the generation of liposomes. Thus, in one embodiment, sonication, extrusion, and Mozafari methods may be employed to produce liposomes. In one embodiment, liposomes may be made using Phospholipon 901, Phospholipon 10011, dipalmitoylphosphatidylcholine (DPPC), stearylamine (SA), dicetyl phosphate (DCP), cholesterol, or a combination thereof.

Methods of Producing Nanoliposomes

In on embodiment, in order to separate the liposomes, the particles are fractionated by successive centrifugations, each run at 4.degree. C., for 40 minutes at the g force of 1.3.times.10.sup.5, as follows: The pellet after 3 runs is the microparticle-enriched fraction, the supernatant of the microparticle enriched fraction subjected to 3 additional runs is the nanoparticle-enriched fraction.

In one embodiment, the liposomes may be lyophilized.

Methods of Producing a Polymer-Conjugated Lipid

In one embodiment, a crosslinking reagent is used to link a polymer to a lipid. In one embodiment, the crosslinking reagents comprise glutaraldehyde (GAD), a water soluble carbodiimide, which in one embodiment is 1-ethyl-3-(3-dimethylaminopropyl) carbodiimide (EDC), genipin, transglutaminase, formaldehyde or a combination thereof.

In one embodiment, a polymer is conjugated to a lipid directly or via a linker. In one embodiment, the linker is a glutaryl linker, which in one embodiment, is represented by the following formula: —OC(CH$_2$)$_3$CO—. In another embodiment, —CO-alkylene-CO, —NH-alkylene-NH—, —CO-alkylene-NH—, —NH-alkylene-NHCO-alkylene-NH—, an amino acid, cycloalkylene, wherein alkylene in each instance, is straight or branched chain and comprises 2 or more, preferably 2 to 30 atoms in the chain, —(—O—CH(CH$_3$CH$_2$—)$_x$—, wherein x is an integer of 1 or more.

In one embodiment, the linkage between the polymer, in one embodiment, a polysaccharide, and the lipid, in one embodiment a phospholipids, is an amide linkage. In another embodiment, the linkage between the polysaccharide and the phospholipid is an ester linkage.

Figure 4:
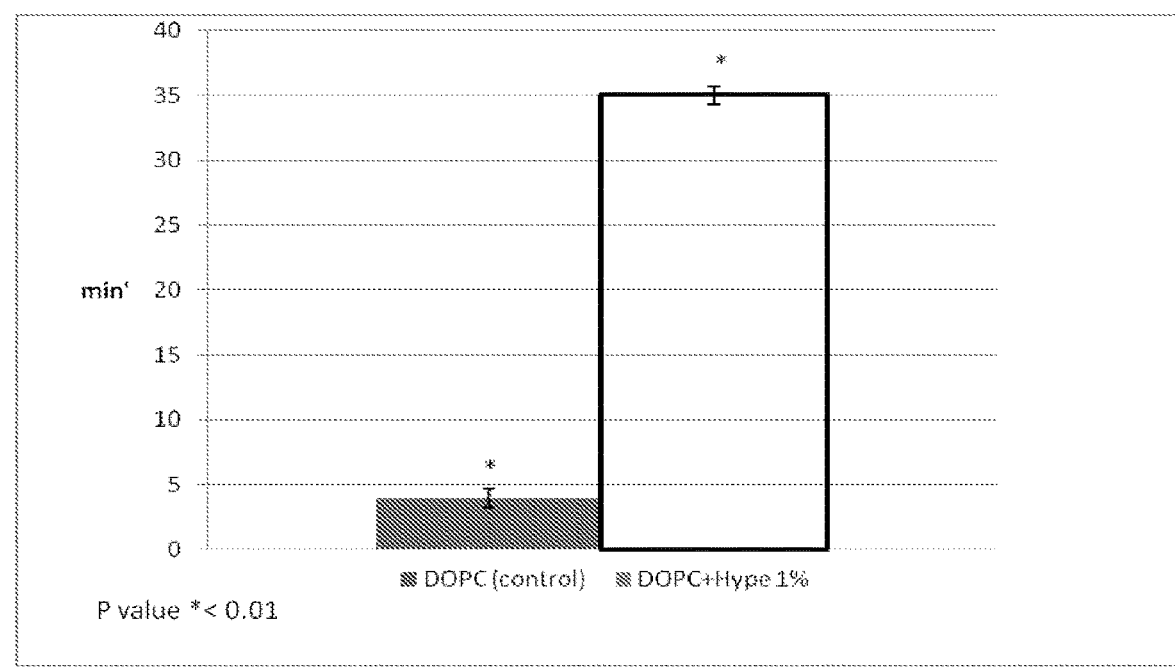
FIG. 4: Po-L inhibits liposome decomposition by external $PLA_2$. Liposomes composed of di-oleoyl-phosphatidyl-choline (DOPC) and PC labeled with $C_6$-NBD (a fluorescent fatty acid) at carbon 2, with or without HyPE, were interacted with external phospholipase A2 (PLA2). The hydrolysis of liposomal phospholipids was determined by the release of the fluorescence intensity of C6-NBD-fatty acid PC release by the PLA2 action. The figure depicts the time required to hydrolyze 5% of the liposomal C6-NBD-PC (representing the total liposomal phospholipids).

In one embodiment, polymer-conjugated lipids are combined with liposomes in solution, wherein the lipid component of the polymer-conjugated lipids integrates into the lipid bilayer of the liposomes. In one embodiment, the polymers anchored to the surface of the liposome via the covalently bound lipids radiate from the liposome surface (i.e., perpendicular to the liposome surface) like a mushroom (FIG. 1a). In one embodiment, the mushroom structure results from a comparatively low Po-L/liposome ratio, wherein the Po-Ls are less densely packed. In one embodiment, the polymers anchored to the surface of the liposome via the covalently bound lipids radiate from the liposome surface (i.e., perpendicular to the liposome surface) like a brush (FIG. 1b). In one embodiment, the brush structure results from a comparatively high Po-L/liposome ratio, wherein the Po-Ls are crowded together. In one embodiment, the Po-L/liposome ratio is adjusted so that there is an intermediate structure, a mushroom-brush structure, which in one embodiment, provides a protection of approximately 3-10 nm. In one embodiment, the lipid-conjugated polymers form a protective layer of approximately 3-10 nm (FIGS. 1a-1b), which, in one embodiment, protects the liposome from degrading enzymes or other injurious/lytic agents, such as phospholipase A2 (PLA2), as was demonstrated herein (FIG. 4). In another embodiment, the lipid-conjugated polymers form a layer greater than 1 nm on the liposome. In another embodiment, the lipid-conjugated polymers form a layer of approximately 3.5 nm. In another embodiment, the lipid-conjugated polymers form a layer of approximately 4.5 nm. In another embodiment, the lipid-conjugated polymers form a layer of approximately 3.5-4.5 nm. In another embodiment, the lipid-conjugated polymers form a layer of approximately 3-5 nm. In another embodiment, the lipid-conjugated polymers form a layer of approximately 2-7 nm. Lipid-conjugated polymers are known in the art to act as PLA2 inhibitors, and the data presented herein demonstrates that lipid-conjugated polymers can also protect liposomes from degradation.

This is in contrast to large polysaccharides, such as native, non-truncated hyaluronic acid, which coat the outer surface of a liposome, forming a layer of approximately 1 nm (FIG. 1c), which is not sufficient to protect liposomes from many enzymes. In addition, it is known in the art that liposomes formed from mixing polymers with lipids even in the presence of crosslinking agents may result in an adhesion of polymers to the surface of said liposomes rather than the integration of polymer-liposome conjugates into the liposome.

Uses of Polymer-Conjugated Lipid Liposomes

In one embodiment, the present invention provides a drug delivery system comprising a liposome comprising a polymer-conjugated lipid.

In another embodiment, the present invention provides a drug delivery system comprising a liposome comprising a lipid bilayer and a polymer-conjugated lipid, wherein said polymer-conjugated lipid is incorporated into said lipid bilayer.

In another embodiment, the present invention provides a drug delivery system comprising a liposome comprising two or more polymer-conjugated lipids, wherein said polymer-conjugated lipid comprises two or more lipids conjugated to a single polymer.

In another embodiment, the present invention provides a drug delivery system comprising a liposome comprising two or more low molecular weight glycosaminoglycan (GAG)-conjugated lipids, wherein said low molecular weight GAG-conjugated lipid comprises two or more lipids conjugated to a single GAG.

In another embodiment, the present invention provides a drug delivery system comprising a liposome comprising a polymer-conjugated lipid, wherein said polymer is not a glycosaminoglycan.

In one embodiment, the polymer-conjugated lipid increases the stability of the liposome, which in one embodiment, comprises a bioactive drug. In another embodiment, the polymer-conjugated lipid decreases degradation of the liposome. In another embodiment, the polymer-conjugated lipid increases the half-life of the liposome. In another embodiment, the liposome targets the bioactive polymer-conjugated lipid to inflamed tissue, thereby increasing the effectiveness of the polymer-conjugated lipid. In one embodiment, the liposome comprising the bioactive polymer-conjugated lipid further comprises an additional bioactive drug. In one embodiment, the liposome targets inflamed tissue due to its size, which allows it to enter inflamed but is not able to enter non-inflamed tissue.

In one embodiment, any of the liposomes of and for use in the methods of this invention comprises one or more polymer-conjugated lipids of the present invention. Thus, in one embodiment, a liposome of the present invention comprises HyPE and KSPE. In another embodiment, a liposome of the present invention comprises CSAPE and PEG-PE. In another embodiment, a liposome of the present invention comprises HyPE and PEG-PE. It is to be understood that a liposome of the present invention may comprise two, three, four, or more different polymer-conjugated lipids of the present invention integrated into a lipid bilayer of said liposome.

In one embodiment, the liposomes of the present invention comprise a hydrophobic agent in the lipid layer.

In another embodiment, the liposomes of the present invention comprise a hydrophilic agent encapsulated within the liposome.

In one embodiment, the agent is a nucleic acid, such as plasmid DNA, short interfering RNA (siRNA), short-hairpin RNA, small temporal RNA (stRNA), microRNA (miRNA), RNA mimetics, or heterochromatic siRNA condensed with a cationic peptide, such as a protamine sulfate and polylysine or a cationic polymer, such as polyethyleneimine (PET), polyamine spermidine, and spermine.

In one embodiment, compositions of the present invention may be used as microscopic drug delivery systems (MDDS). In another embodiment, compositions of the present invention provide sustained or controlled release of therapeutic or diagnostic drugs. In another embodiment, compositions of the present invention reduce drug degradation or inactivation. In another embodiment, compositions of the present invention improve drug efficacy and allow reduction in the frequency of dosing of a drug. In another embodiment, compositions of the present invention reduce toxicity and undesirable side effects of a drug. In another embodiment, compositions of the present invention encapsulate drugs for subsequent delivery for use in therapy and diagnosis. In another embodiment, compositions of the present invention improve the efficiency and decrease the side effects of drugs, vaccines, cosmetics, slimming agents or nutraceuticals. In another embodiment, compositions of the present invention are able to incorporate and protect various types of bioactives as well as deliver them to the target site inside the human or animal body.

In one embodiment, small molecules, such as antibiotics and chemotherapeutic drugs, and large molecules, such as proteins, can be encapsulated in the modified liposomes described herein. In another embodiment, the modified liposomes can be used to encapsulate DNA, and the larger the modified liposomes may even encapsulate whole cells and cell lines. Thus, the modified liposomes can also be used as a scaffold for tissue engineering.

In another embodiment of the present invention, other molecules may be attached first to the polysaccharide, which is then reacted with lipids. These particles have the other molecules appearing on the outside of the particles. These other molecules may be, for example, antibodies, folate, porphyrins, or lectins, and may be used for targeting. In another embodiment, a targeting agent may be attached to the polysaccharide, which in one embodiment is a specific monoclonal antibody, scFv, Fab fragment, receptor ligand, or combination thereof.

In one embodiment, a polysaccharide of the present invention may be conjugated with antibodies against MUC1, MUC2, or MUC3 for targeting to tumors of breast, lung, and prostate cancers. Alternately, a polysaccharide of the present invention may be conjugated with antibodies against ganglioside GM3 for targeting to melanoma.

In one embodiment, the present invention provides a method for encapsulating one or more agents in a liposome. The method comprises the steps of: (1) providing a lyophilized liposome having lipids conjugated with a polymer, wherein the polymer is covalently linked to the lipid (2) providing a hydrophilic agent in aqueous solution; and (3) rehydrating the lyophilized liposome with the aqueous solution comprising the hydrophilic agent. In one embodiment, the polymer-conjugated lipid may further comprise a targeting moiety covalently linked to the polymer-conjugated lipid.

The present invention also provides kits for making liposomes comprising polymer-conjugated lipids and as well as kits for drug and/or agent encapsulation comprising a liposome and a polymer-conjugated lipid.

In another embodiment, the present invention provides a method for treating a subject suffering from a pathological condition, comprising administering to said subject a bioactive agent encapsulated in a liposome comprising a polymer-conjugated lipid.

In another embodiment, the present invention provides a method for treating, inhibiting, or suppressing a pathological condition in a subject, comprising administering to said subject a bioactive agent encapsulated in a liposome comprising a polymer-conjugated lipid.

In another embodiment, the present invention provides a method for treating, inhibiting, or suppressing a pathological condition in a subject, comprising administering to said subject a liposome comprising a lipid bilayer and a polymer-conjugated lipid, wherein said polymer-conjugated lipid is incorporated into said lipid bilayer. In one embodiment, the liposome comprises an agent that is effective in treating, inhibiting, or suppressing said pathological condition.

In another embodiment, the present invention provides a method for treating, inhibiting, or suppressing a pathological condition in a subject, comprising administering to said subject a bioactive agent encapsulated in a liposome comprising two or more polymer-conjugated lipids, wherein said polymer-conjugated lipid comprises two or more lipids conjugated to a single polymer.

In another embodiment, the present invention provides a method for treating, inhibiting, or suppressing a pathological condition in a subject, comprising administering to said subject a bioactive agent encapsulated in a liposome comprising two or more low molecular weight glycosaminoglycan (GAG)-conjugated lipids, wherein said low molecular weight GAG-conjugated lipid comprises two or more lipids conjugated to a single GAG.

In another embodiment, the present invention provides a method for treating, inhibiting, or suppressing a pathological condition in a subject, comprising administering to said subject a bioactive agent encapsulated in a liposome comprising a polymer-conjugated lipid, wherein said polymer is not a glycosaminoglycan.

In one embodiment, the therapeutic or prophylactic effect of the liposome is due to the natural targeting of nanoliposomes to inflamed tissue. According to this aspect and in one embodiment, a nanoliposome targets the polymer-conjugated lipid to inflamed tissue where the polymer-conjugated lipid exerts an anti-inflammatory effect, thereby initiating a therapeutic or prophylactic effect in the subject. In another embodiment, the liposome comprises a bioactive agent, and the improved effect of the compositions and methods of the present invention is due to the protection from degradation endowed by the polymer-conjugated lipid on the liposome, thereby increasing the half-life of the liposome in a subject, thereby enhancing its effect on said subject. In another embodiment, the improved effect of the compositions and methods of the present invention is due to the slower release of the bioactive agent from the liposome due to the presence of polymer-conjugated lipids integrated into a lipid bilayer of the liposome.

In one embodiment, the pathological condition is sepsis.

In another embodiment, the pathological condition is an intestinal disease, which in one embodiment, is Crohn's Disease, ulcerative colitis, immuno-inflammatory intestinal injury, drug-induced enteropathy, ischemia-induced intestinal injury, inflammatory bowel disease, or a combination thereof.

In another embodiment, the pathological condition is a disease or disorder of the central nervous system or the peripheral nervous system associated with an inflammatory response, which in one embodiment, is multiple sclerosis, Amyotrophic Lateral Sclerosis (ALS), meningitis, demyelinating diseases of the central and peripheral nervous system, or any combination thereof, wherein said demyelinating diseases of the central and peripheral nervous system comprise multiple sclerosis, idiopathic demyelinating polyneuropathy or Guillain-Barr⁻ syndrome, Alzheimer's disease, pain, Huntington's disease (HD), myasthenia gravis (MG), HIV-associated dementia, fronto-temporal dementia (FID), stroke, traumatic brain injury, age-related retinal degeneration, encephalomyelitis, chronic inflammatory demyelinating polyneuropathy, cerebral ischemia-induced injury, or a combination thereof.

In another embodiment, the pathological condition is an obstructive respiratory disease, which in one embodiment, is asthma, chronic obstructive pulmonary disease, or a combination thereof.

In another embodiment, the pathological condition is a dermatological condition, which in one embodiment, is psoriasis, seboreic dermatitis, contact dermatitis, atopic dermatitis, or a combination thereof.

In another embodiment, the pathological condition is an infection. In one embodiment, the infection is viral. In one embodiment, the viral infection is an influenza infection, an HIV infection, or a poxvirus infection. In another embodiment, the infection is bacterial. In one embodiment, the bacterial infection is a *Chlamydia* infection.

In another embodiment, the pathological condition is a neoplasia. In another embodiment, the pathological condition is sarcoma, an adenocarcinoma, colon carcinoma, melanoma, breast carcinoma, leukemia, lymphoma, gastric carcinoma, glioblastoma, astrocytoma, bladder carcinoma, pleural mesothelioma, oat cell carcinoma, bronchogenic carcinoma, or a combination thereof.

In another embodiment, the present invention provides a method for treating, inhibiting or suppressing a disease, condition or disorder in a subject, comprising administering to said subject a bioactive agent encapsulated in a liposome of the present invention. In one embodiment, the condition is conjunctivitis, which in one embodiment, is viral and in another embodiment, is bacterial. In another embodiment, the conjunctivitis is due to an allergen or to an irritant.

In another embodiment, the pathological condition is cystic fibrosis.

In one embodiment, the pathological condition is cancer and said bioactive agent is an anticancer drug. In one embodiment, the cancer is a metastatic cancer. In another embodiment, the pathological condition is an infection, which in one embodiment, is a bacterial infection, a fungal infection, a viral infection, or a parasitic infection. In one embodiment, the bioactive agent is an antibacterial drug, an antifungal drug, an antiviral drug or an antiparasitic drug. In another embodiment, the pathological condition is a prion infection.

In one embodiment, the drug is administered orally, intravenously, intranasally, intraocularly, intramuscularly, or subcutaneously or topically.

In one embodiment, "treating" refers to either therapeutic treatment or prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment. "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of the subject viral infection, while in one embodiment, "secondary" refers to a symptom that is derived from or consequent to a primary cause. In one embodiment, the compositions and methods for use in the present invention treat primary or secondary symptoms or secondary complications related the pathological condition.

In some embodiments, any of the liposomes of and for use in the methods of this invention will comprise one or more polymer-conjugated lipids of the present invention, in any form or embodiment as described herein. In some embodiments, any of the liposomes of this invention will consist of one or more polymer-conjugated lipids of the present invention, in any form or embodiment as described herein. In some embodiments, the liposomes of this invention will consist essentially of one or more polymer-conjugated lipids of the present invention, in any form or embodiment as described herein.

In some embodiments, the term "comprise" refers to the inclusion of a polymer-conjugated lipid, such as HyPE, as well as inclusion of other lipids or lipid conjugates that may be known in the art. In some embodiments, the term "consisting essentially of" refers to a liposome, whose only variation from a standard liposome is the indicated inclusion of a polymer-conjugated lipid, however, other lipids or lipid conjugates may be included that are not involved directly in the improved drug release profile of the liposome. In some embodiments, the term "consisting" refers to a liposome, which contains only a particular a polymer-conjugated lipid, or alternatively, only the recited polymer-conjugated lipids integrated into the liposome.

In one embodiment, the term "targeting agent" or "targeting moiety" refers to an agent that homes in on or preferentially associates or binds to a particular tissue, cell type, receptor, infecting agent or other area of interest. Examples of a targeting agent include, but are not limited to, an oligonucleotide, an antigen, an antibody or functional fragment thereof, a ligand, a receptor, one member of a specific binding pair, a polyamide including a peptide having affinity for a biological receptor, an oligosaccharide, a polysaccharide, a steroid or steroid derivative, a hormone, e.g., estradiol or histamine, a hormone-mimic, e.g., morphine, or other compound having binding specificity for a target. In the methods of the present invention, the targeting agent promotes transport or preferential localization of the lipid particle of the present invention to the target of interest.

As used herein, an "antibody" or "functional fragment" of an antibody encompasses polyclonal and monoclonal antibody preparations, as well as preparations including hybrid or chimeric antibodies, such as humanized antibodies, altered antibodies, F(ab').sub.2 fragments, F(ab) fragments, Fv fragments, single domain antibodies, dimeric and trimeric antibody fragment constructs, minibodies, and functional fragments thereof which exhibit immunological binding properties of the parent antibody molecule and/or which bind a cell surface antigen.

The targeting agent can be any ligand the receptor for which is differentially expressed on the target cell. Non-limiting examples include transferrin, folate, other vitamins, EGF, insulin, Heregulin, RGD peptides or other polypeptides reactive to integrin receptors, antibodies or their fragments. Sugar molecules or glycoproteins, lipid molecules or lipoproteins may be targeting agents.

In one embodiment, antibodies against cell surface markers that am specifically expressed in disease states can be used as targeting agent. Examples of antigens that specifically appear in tumors cells include ganglioside GM3 on melanoma, MUC1, MUC2, and MUC3 on the surface of breast cancer, lung cancer and prostate cancer, and Lewis X on the surface of gastro-intestinal digestive cancer. In one embodiment the antibody is a functional fragment containing the antigen binding region of the antibody. A preferred antibody fragment is a single chain Fv fragment of an antibody. The antibody or antibody fragment is one which will bind to a receptor on the surface of the target cell, and preferably to a receptor that is differentially expressed on the target cell. In one embodiment, multiple types of targeting agents may be covalently attached to the lipid particle.

In another embodiment, the present invention provides a method for performing diagnostic imaging in a subject, comprising the step of administering a diagnostic agent encapsulated in a liposome comprising a polymer-conjugated lipid.

In another embodiment, the present invention provides a method for performing diagnostic imaging in a subject, comprising the step of administering a diagnostic agent encapsulated in a liposome comprising a lipid bilayer and a polymer-conjugated lipid, wherein said polymer-conjugated lipid is incorporated into said lipid bilayer to said subject and imaging said patient.

In another embodiment, the present invention provides a method for performing diagnostic imaging in a subject, comprising the step of administering a diagnostic agent encapsulated in a liposome comprising two or more polymer-conjugated lipids, wherein said polymer-conjugated lipid comprises two or more lipids conjugated to a single polymer.

In another embodiment, the present invention provides a method for performing diagnostic imaging in a subject, comprising the step of administering a diagnostic agent encapsulated in a liposome comprising two or more low molecular weight glycosaminoglycan (GAG)-conjugated lipids, wherein said low molecular weight GAG-conjugated lipid comprises two or more lipids conjugated to a single GAG.

In another embodiment, the present invention provides a method for performing diagnostic imaging in a subject, comprising the step of administering a diagnostic agent encapsulated in a liposome comprising a polymer-conjugated lipid, wherein said polymer is not a glycosaminoglycan.

In another embodiment, the present invention provides a method for inhibiting PLA2 in a subject comprising the step of administering to said subject a liposome comprising a polymer-conjugated lipid.

In another embodiment, the present invention provides a method for inhibiting PLA2 in a subject comprising the step of administering to said subject a liposome comprising two or more polymer-conjugated lipids, wherein said polymer-conjugated lipid comprises two or more lipids conjugated to a single polymer.

In another embodiment, the present invention provides a method for inhibiting PLA2 in a subject comprising the step of administering to said subject a liposome comprising two or more low molecular weight glycosaminoglycan (GAG)-conjugated lipids, wherein said low molecular weight GAG-conjugated lipid comprises two or more lipids conjugated to a single GAG.

In another embodiment, the present invention provides a method for inhibiting PLA2 in a subject comprising the step of administering to said subject a liposome comprising a polymer-conjugated lipid, wherein said polymer is not a glycosaminoglycan.

In one embodiment, the terms "encapsulation" and "entrapped," as used herein, refer to the incorporation of an agent in a lipid particle. The agent is present in the aqueous interior of the lipid particle. In one embodiment, a portion of the encapsulated agent takes the form of a precipitated salt in the interior of the liposome. The agent may also self precipitate in the interior of the liposome.

In one embodiment, "agent" means any agent or compound that can affect the body therapeutically, or which can be used in vivo for diagnosis. Examples of therapeutic agents include chemotherapeutics for cancer treatment, antibiotics for treating infections, antifungals for treating fungal infections, therapeutic nucleic acids including nucleic acid analogs, e.g., siRNA. In one embodiment, the agent of interest is a gene, polynucleotide, such as plasmid DNA, DNA fragment, oligonucleotide, oligodeoxynucleotide, antisense oligonucleotide, chimeric RNA/DNA oligonucleotide, RNA, siRNA, ribozyme, or viral particle. In one embodiment, the agent is a growth factor, cytokine, immunomodulating agent, or other protein, including proteins which when expressed present an antigen which stimulates or suppresses the immune system. In one embodiment, the agent is a diagnostic agent capable of detection in vivo following administration. Exemplary diagnostic agents include electron dense material, magnetic resonance imaging agents, radiopharmaceuticals and fluorescent molecules. Radionucleotides useful for imaging include radioisotopes of copper, gallium, indium, rhenium, and technetium, including isotopes $^{64}$Cu, $^{67}$Cu, $^{111}$In, $^{99m}$Tc, $^{67}$Ga or $^{68}$Ga. Imaging agents disclosed by Low et al. in U.S. Pat. No. 5,688,488, incorporated herein by reference, are useful in the liposomal complexes described herein.

In one embodiment, the agent of interest is a nucleic acid. e.g., DNA, RNA, siRNA, plasmid DNA, short-hairpin RNA, small temporal RNA (stRNA), microRNA (miRNA), RNA mimetics, or heterochromatic siRNA. The nucleic acid agent of interest has a charged backbone that prevents efficient encapsulation in the lipid particle. Accordingly, the nucleic acid agent of interest may be condensed with a cationic polymer, e.g., PEI, polyamine spermidine, and spermine, or cationic peptide, e.g., protamine and polylysine, prior to encapsulation in the lipid particle, in one embodiment, the agent is not condensed with a cationic polymer.

In one embodiment, the agent of interest is encapsulated in the lipid particle in the following manner. The lipid particle, including a cryoprotectant and a targeting agent is provided lyophilized. The agent of interest is in an aqueous solution. The agent of interest in aqueous solution is utilized to rehydrate the lyophilized lipid particle. Thus, the agent of interest is encapsulated in the rehydrated lipid particle.

In one embodiment, two agents of interest may be delivered by the lipid particle. One agent is hydrophobic and the other is hydrophilic. The hydrophobic agent may be added to the lipid particle during formation of the lipid particle. The hydrophobic agent associates with the lipid portion of the lipid particle. The hydrophilic agent is added in the aqueous solution rehydrating the lyophilized lipid particle.

Any suitable lipid:pharmaceutical agent ratio that is efficacious is contemplated by this invention. In one embodiment, lipid:pharmaceutical agent molar ratios include about 2:1 to about 30:1, about 5:1 to about 100:1, about 10:1 to about 40:1, about 15:1 to about 25:1.

In one embodiment, the loading efficiency of pharmaceutical agent is a percent encapsulated pharmaceutical agent of about 50%, about 60%, about 70% or greater. In one embodiment, the loading efficiency for a hydrophilic agent is a range from 50-100%. The preferred loading efficiency of pharmaceutical agent associated with the lipid portion of the lipid particle, e.g., a pharmaceutical agent poorly soluble in aqueous solution, is a percent loaded pharmaceutical agent of about 50%, about 60%, about 70%, about 80%, about 90%, about 100%. In one embodiment, the loading efficiency for a hydrophobic agent in the lipid layer is a range from 80-100%.

In one aspect of the method, the liposome product is detectably labeled with a label selected from the group including a radioactive label, a fluorescent label, a non-fluorescent label, a dye, or a compound which enhances magnetic resonance imaging (MRI). In one embodiment, the liposome product is detected by acoustic reflectivity. The label may be attached to the exterior of the liposome or may be encapsulated in the interior of the liposome.

In another embodiment, the present invention provides a method of delivering a nucleic acid to a subject comprising the step of administering said nucleic acid encapsulated in a liposome comprising a lipid bilayer and a polymer-conjugated lipid, wherein said polymer-conjugated lipid is incorporated into said lipid bilayer to said subject.

In another embodiment, the present invention provides a method of delivering a nucleic acid to a subject comprising the step of administering said nucleic acid encapsulated in a modified liposome comprising a lipid bilayer, wherein said liposome comprises two or more polysaccharide-conjugated phospholipids (PoS-PL s) incorporated into said lipid bilayer to said subject.

It is still another object of the present invention to provide gene delivery using lipid particles as the gene delivery materials. For example, the mutant Raf gene can be targeted and delivered to tumor cells for anti-angiogenic purposes; the gene for the highly toxic cytokine TNF-alpha may be delivered to cancers to promote cell death; genes for the cytokines IL-12 and IFN-.gamma. can be delivered to the lungs for allergy-induced hyperesponsiveness (AHR); and the cDNA for the glial cell line derived neurogrowth factor (GDNF) may be targeted to the dopamine cells at the substantia nigra in Parkinson's disease patients.

In one embodiment, liposomes of the present invention are used to deliver anti-cancer agents. In one embodiment, liposomes comprising HYPE and containing a mitotic inhibitor such as Paclitaxel is encompassed in the compositions and related methods of the present invention. In one embodiment, numerous human tumor types, including ovarian cancer, breast cancer, non-small cell lung cancer, colorectal cancer, head and neck cancers, and other malignancies, have a significant expression of the CD44 family of cell-surface proteoglycans. For example, the CD44 proteoglycan family is expressed in as many as about 90% of fresh samples from primary human ovarian tumors or peritoneal implants. Additionally, studies with squamous cell carcinomas of the head and neck have shown up to 75% to have expression of CD44. Typically, epithelial cancer stem cells also express CD44.

The CD44 proteoglycan family includes a parental form and 10 or more isoforms that are major receptors for hyaluronic acid. Hyaluronic acid serves a variety of functions within the extracellular matrix, including direct receptor-mediated effects on cell behavior. These effects occur via intracellular signaling pathways in which hyaluronic acid binds to, and is internalized by, CD44 cell surface receptors.

As used herein, the term "anti-cancer agent" refers to a compound capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the lifespan of a subject with a cancer.

In some embodiments, anti-cancer agents suitable for use in the modified liposomes of the present disclosure comprise a taxane. In general, taxanes typically are diterpenes with antineoplastic properties, such as the inhibition of microtubule function. Examples of suitable taxanes include, but are not limited to, paclitaxel, docetaxel, and derivatives thereof.

In one embodiment, a suitable anti-cancer agent may be present as an active ester, such as a N-hydroxysuccinimide ester ("NHS ester"). For example, in one embodiment, a suitable anti-cancer agent may be paclitaxel-N-hydroxysuccinimide ester, also referred to as "paclitaxel-NHS ester" or "Taxol-NHS ester." In another embodiment, the anti-cancer agent to be delivered using the liposomes of the present invention is Doxorubicin, Topotecan, or a combination thereof.

Other anti-cancer agents may also be suitable for use in the disclosed modified liposomes. Anti-cancer agents include, for example, chemotherapy agents (chemotherapy), radiotherapy agents (radiotherapy), immune therapy agents (immunotherapy), genetic therapy agents (gene therapy), hormonal therapy, other biological agents (biotherapy) and/or alternative therapies. A non-exhaustive list of anti-cancer agents which may be suitable for use as an anti-cancer agent in the modified liposomes disclosed herein may be found in U.S. Pat. No. 7,344,829, column 12, line 43 through column 13, line 4, incorporated herein by reference.

In one embodiment, the present invention provides a composition comprising a liposome of the present invention.

The phrase "therapeutically effective" is intended to qualify the amount of active ingredients used in the treatment of a disease or disorder. This amount will achieve the goal of reducing or eliminating the said disease or disorder.

The pharmaceutical composition of the present invention can be used to treat an indication, i.e., a pathological condition, in a subject in need thereof. The term "subject" as used herein is taken to include humans and other mammals such as cattle, sheep, pigs, goats, dogs, cats, rats, mice, etc., as well as animals including amphibians, birds, reptiles and fish.

The pharmaceutical composition according to the present invention is preferably administered orally but may also be administered by another suitable route, including parenteral, e.g., subcutaneous, intravenous, topical, intramuscular, intraperitoneal, transdermal, rectal, vaginal, intranasal or intraocular. Alternatively or concomitantly, administration may be by the oral route. Oral routes of administration are understood to include buccal and sublingual routes of administration.

Parenteral administration can be by bolus injection or by gradual perfusion over time. Parenteral administration is generally characterized by injection, most typically subcutaneous, intramuscular or intravenous.

Topical formulations composed of the active ingredient of the pharmaceutical composition of the present invention, penetration enhancers, and other biologically active drugs or medicaments may be applied in many ways. A liquid formation can be applied dropwise, from a suitable delivery device, to the appropriate area of skin or diseased skin or mucous membranes and rubbed in by hand or simply allowed to air dry. A suitable gelling agent can be added to the liquid formulation and the preparation can be applied to the appropriate area and rubbed in. For administration to wounds or burns, the active ingredient may be incorporated into dosage forms such as oils, emulsions, and the like. Such preparations may be applied directly to the affected area in the form of lotions, creams, pastes, ointments, and the like.

Alternatively, the topical liquid formulation can be placed into a spray device and be delivered as a spray. This type of drug delivery device is particularly well suited for application to large areas of skin affected by dermal pathologies, to highly sensitive skin or to the nasal or oral cavities. Optionally, the pharmaceutical composition may be administered in the form of an ointment or transdermal patch.

The pharmaceutical composition of the present invention may also be administered by other routes which optimize uptake by the mucosa, e.g., vaginal (especially in the case of treating vaginal pathologies), rectal and intranasal routes of administration. Furthermore, the pharmaceutical composition may be adapted for delivery through mucosal tissue or epithelia. If administered intranasally, the pharmaceutical composition will typically be administered in an aerosol form, or in the form of drops. This may be especially useful for treating lung pathologies.

Suitable formulations can be found in A. Gennaro (2000) "Remington: le Science and Practice of Pharmacy", 20th edition, Lippincott, Williams, & Wilkins: Pharmaceutical Dosage Forms and Drug Delivery Systems (1999) H. C. Ansel et al., eds 7.sup.th ed., Lippincott, Williams, & Wilkins; and Handbook of Pharmaceutical Excipients (2000) A. H. Kibbe et al., eds., 3rd ed. Amer. Pharmaceutical Assoc. each of which is incorporated herein by reference.

Depending on the intended mode of administration, the composition used may be in the form of solid, semi-solid or liquid dosage forms, such as for example, tablets, suppositories, pills, capsules, powders, liquids, suspensions, or the like, preferably in unit dosage forms suitable for single administration of precise dosages. The pharmaceutical composition of the present invention and a pharmaceutically acceptable diluent, carrier, excipient, adjuvant, or auxiliary agent. It is preferred that the pharmaceutically acceptable carrier be one which is chemically inert to the active therapeutic protein and which has no detrimental side effects or toxicity under the conditions of use. The choice of carrier is determined partly by the particular active ingredient, as well as by the particular method used to administer the composition. Accordingly, there are a wide variety of suitable formulations of the pharmaceutical compositions of the present invention.

Suitable excipients are, in particular, fillers such as saccharides (e.g., lactose or sucrose, mannitol, sorbitol, etc.) cellulose preparations and/or calcium phosphates (e.g., tricalcium phosphate, calcium hydrogen phosphate, etc.) as well as binders such as starch paste using, for example, maize starch, wheat starch, rice starch, potato starch, gelatin, tragacanth, methylcellulose, hydroxypropylmethylcellulose, sodium carboxymethylcellulose, and/or polyvinyl pyrrolidine.

Injectable formulations for parenteral administration can be prepared as liquid suspensions, solid forms suitable for solution or suspension in liquid prior to injection, or as emulsions. Suitable excipients are, for example, water, saline, dextrose, glycerol, ethanol or the like. In addition, if desired, the pharmaceutical composition to be administered may also contain minor amounts of non-toxic auxiliary agents such as wetting or emulsifying agents, pH buffering agents and the like, such as for example, sodium acetate, sorbitan monolaurate, triethanolamine oleate, etc.

Aqueous injection suspensions may also contain substances that increase the viscosity of the suspension, including, for example, sodium carboxymethylcellulose, sorbitol, and/or dextran. Optionally, the suspension may also contain stabilizers.

The parenteral formulations can be present in unit dose or multiple dose sealed containers, such as ampules and vials, and can be stored in a freeze-dried (lyophilized) condition requiring only the addition of the sterile liquid carrier, e.g., water, for injections immediately prior to use. Extemporaneous injection suspensions can be prepared from sterile powders, granules, and tablets of the kind previously described.

For oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions include suspensions, tablets, dispersible tablets, pills, capsules, powders, sustained release formulations and the like. Formulations suitable for oral administration can consists of liquid suspensions such as effective amounts of the drug encapsulating gagomer particles suspended in diluents such as water, saline, or orange juice; sachets, lozenges, and troches, each containing a predetermined amount of the active ingredient as solids or granules; powders, suspensions in an appropriate liquid; and suitable emulsions. Liquid formulations may include diluents such as water and alcohols, e.g., ethanol, benzyl alcohol, and the polyethylene alcohols, either with or without the addition of a pharmaceutically acceptable surfactant, suspending agents, or emulsifying agents.

When the composition is a pill or tablet, it will contain, along with the active ingredient, a diluent such as lactose, sucrose, dicalcium phosphate, or the like; a lubricant such as magnesium stearate or the like; and a binder such as starch, gum acacia, gelatin, polyvinylpyrrolidine, cellulose and derivatives thereof, and the like.

Tablet forms can include one or more of lactose, sucrose, mannitol, corn starch, potato starch, alginic acid, microcrystalline cellulose, acacia, gelatin, guar gum, colloidal silicon dioxide, crosscarmellose sodium, talc, magnesium stearate, calcium stearate zinc stearate, stearic acid, preservatives, flavoring agents, pharmaceutically acceptable disintegrating agents, moistening agents, and pharmacologically compatible carriers.

Capsule forms can be of the ordinary hard- or soft-shelled gelatin type containing, for example, surfactants, lubricant, and inert fillers, such as lactose, sucrose, calcium phosphate, and corn starch.

Lozenge forms can contain the drug encapsulating gagomer particles in a carrier, usually sucrose and acacia or tragacanth, as well as pastilles comprising the active ingredient in an inert base such as gelatin or glycerin, or sucrose and acacia.

The amount of the active ingredient in the pharmaceutical composition of the present invention to be administered to any given patient must be determined empirically, and will differ depending upon the condition of the patients. Relatively small amounts of the pharmaceutical composition can be administered at first, with steadily increasing dosages if no adverse effects are noted. Of course, the maximum safe toxicity dosage as determined in routine animal toxicity tests should never be exceeded.

Pharmaceutical compositions within the scope of the present invention include all compositions wherein the active ingredient is contained in an amount effective to achieve its intended purpose. While individual needs vary, determination of optimal ranges of effective amounts of each compound is within the skill of the art. The dosage administered will depend upon the age, health, and weight of the individual recipient thereof as well as upon the nature of any concurrent treatment and the effect desired. Typical dosages include 0.01 to 100 mg/kg body weight. The preferred dosages are in the range of about 0.1 to 100 mg/kg body weight. The most preferred dosages are in the range of about 1 to 50 mg/kg body weight.

Example 1

Preparation of Polymer-Conjugated Lipids (Po-Ls)
Hyaluronic Acid-Conjugated Di-Palmitoyl Phosphatidylethanolamine (HyPE)

20.0 g Hyaluronic Acid was dissolved in 770 ml of the 0.1 M MES buffer (adjusted with 5N NaOH to pH=6.4) while stirring and heating to 35° C. (Solution 1), 2.00 g of di-palmitoyl phosphatidylethanolamine (DPPE) was dissolved in a mixture of 750 ml tert-butanol (93% t-BuOH, 7% water) and 65 ml of water while stirring and heating to 50° C. until complete dissolution of the DPPE was achieved (Solution 2).

Solution 2 was added to Solution 1 under stirring, 2.00 g HOBT was added and the mixture was allowed to cool to 30±5° C. 20 g EDAC was added and when dissolved (1-2 minutes) the reaction mixture was transferred to a 2 liter RB flask.

The reaction mixture was sonicated in an ultrasound bath for 3 hours. On completion of the sonication step, the reaction mixture was kept stirring overnight at room temperature.

Haemaccel-Conjugated Di-Palmitoyl Phosphatidylethanolamine (HemPE)
Hem NH Preparation 4 g Hexanediamine was dissolved in 400 ml $H_2O$ and then titrated with HCl to pH=6.0. 500 ml of 3.5% Haemaccel and 2 g EDAC was added. The pH was maintained at 6.0 for 3-4 h by titration and the reaction was left overnight. The pH was adjusted the following morning to 6.0, 0.5 g EDAC was added, and the reaction was continued for 4 h. The solution was acidified to pH 3.0-4.0 and filtered through a 10 kD Filtron.

Binding of Hem-NH to Glutaryl-PE (Glu-PE)

200 mg Glu-PE was dissolved in C/M:1/1, and the solution was activated with 800 mg DCC for 1.5 h. The solvents were evaporated in a rotor vacuum. A solution of 1 g Hem-Nh dissolved in 40 ml $H_2O$ containing 1 ml DiDAB and 0.5 ml Triethylamine was immediately added. The reaction was allowed to proceed for 48 h. The resulting solution was washed with DCM/MeOH/EtOH to remove free Glu-PE. The aqueous phase was dialysed against water and lyophilized. Dissolved in $H_2O$/MeOH:1/1, passed through an ion exchange column (Amberlite IR 120). Dialysed against water, lyophilized.

Preparation of the Liposomes

Unilamellar liposomes were prepared from lipids, such as DMPC or egg-PC with/without 33 mole % cholesterol, dissolved in tert-butanol, were lyophilized to dryness, suspended in tris-buffer, pH=7.4, and subjected to extrusion through a polycarbonate filter, to obtain nano-liposomes sized between 50-100 nm average diameter, according to a published procedure (MacDonald et al., 1991). To obtain Po-L/lipid liposomes, the lipid suspensions were mixed with Po-L solutions (e.g., HyPE or Hem-PE in buffer) at the desired ratio, prior to extrusion. The size of the mixed nano-liposomes was determined by dynamic light scattering.

Results

Figure 2:
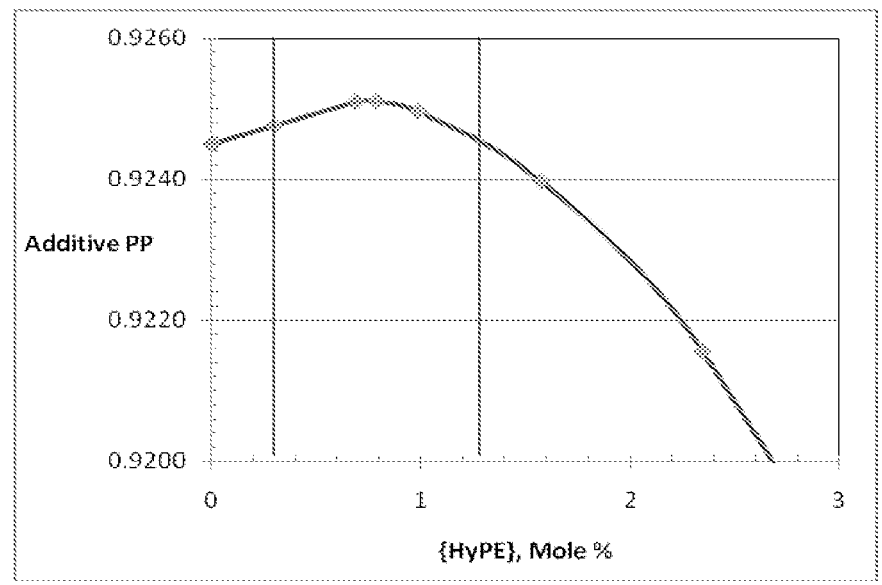
FIG. 2: Effect of HyPE on the stability of liposomes composed of EggPC:Chol:HyPE, expressed by the change in the Additive Packing Parameter (PP) of the liposomes: The figure shows the PP as a function of mole percent of PE conjugated to HyPE in the liposomes. Optimal stability is obtained when PP is close to 1.0 (but not higher than 1). The vertical lines show the HyPE concentrations that increase the liposome stability. EggPC=egg phosphatidyl-choline; Chol=Cholesterol; HyPE=Hyaluronic acid (HA)-conjugated phosphatidyl-ethanolamine (PE).

Po-L/Lipid form nano-liposomes of 100-130 nm, suitable for selective penetration of the inter-cellular space of inflamed tissues, while avoiding penetration into healthy tissues, with a packing parameter of 0.8 (stable range=0.74-1.0). FIG. 2 shows the mole percent of PE conjugated to HyPE in the liposomes needed to obtain optimal stability for PE-HyPE liposomes, which is obtained when the packing parameter (PP) is close to 1.0 (but not higher than 1).

Figure 3:
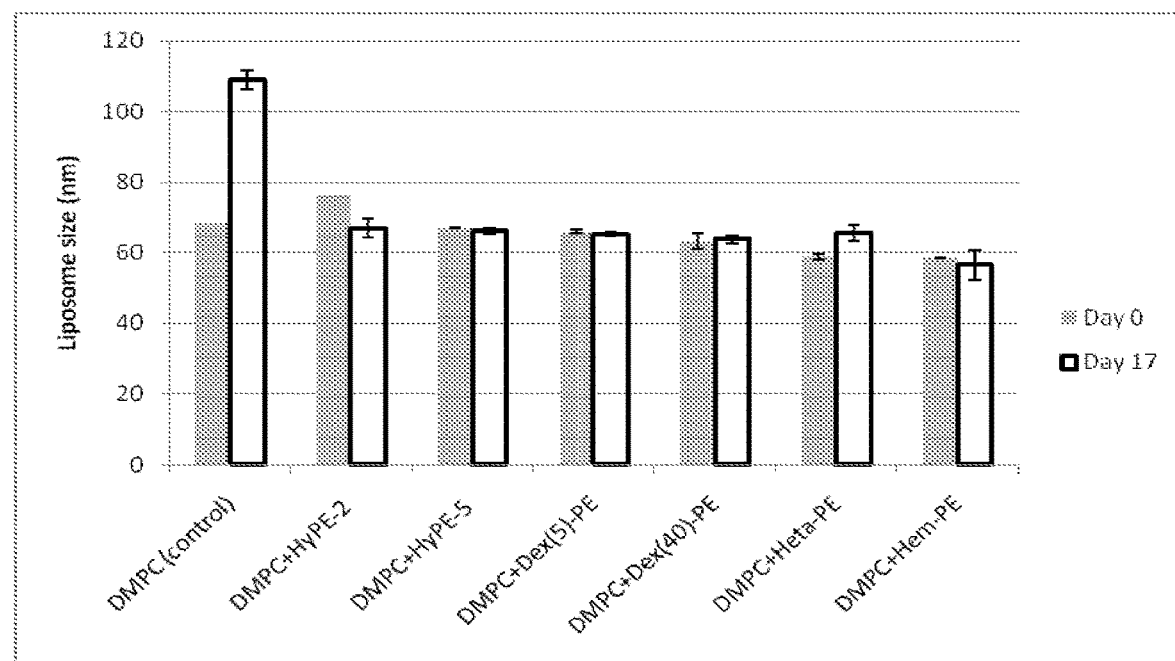
FIG. 3: Size stability of liposomes with different polymer-conjugated lipids (Po-Ls): Liposomes with or without the indicated Po-L were incubated at 55° C. for 17 days, and the change in their size was monitored using dynamic light scattering. The diagram shows the sizes (nm) at day 1 and 17. DMPC=dimyristoyl phosphatidyl-choline; HyPE=HyPE=Hyaluronic acid (HA)-conjugated Phosphatidyl-ethanolamine (PE); Dex (5)-PE=Dextran (MW 5K)-conjugated PE; Dex(40)=Dextran (MW 40K)-conjugated PE; Heta-PE=Hetastarch (hydroxyethylstarch)-conjugated PE; Hem-PE=Hemaccel (Polygeline)-conjugated PE.

The size of Po-L/Lipid nanoliposomes was stable at 60° C. for at least 27 days (data not shown), while the size of bare lipid dimyristoyl phosphatidyl-choline (DMPC) nanoliposomes (control) increased by day 17 (FIG. 3) and began decreasing at day 20 (data not shown). Nanoliposomes comprising 1.6% HyPE-2, 0.6% HyPE-5, Dex(5)-PE, Dex(40)-PE, Heta-PE, and Hem-PE all had more stable nanoliposome size than control nanoliposomes (FIG. 3). HyPE-2 and HyPE-5 describe the molar ratio of hyaluronic acid to PE in those conjugates, which can also be described as the number of hyaluronic acid disaccharide units per PE (Table 2).

TABLE 2

Composition of two HyPE batches, tested for their effect on the size stability of Po-L-containing DMPC liposomes (as in FIG. 3).

| Batch of HyPE | PE/HA* (mol/mol) | **DSU/PE (mole/mole) |
|---|---|---|
| HyPE-2 | 2-3 | 62 |
| HyPE-5 | 5 | 28 |

*-HA Average MW=50 KD; **DSU=HA Disaccharide Units (MW=379) in HyPE

Figure 5:
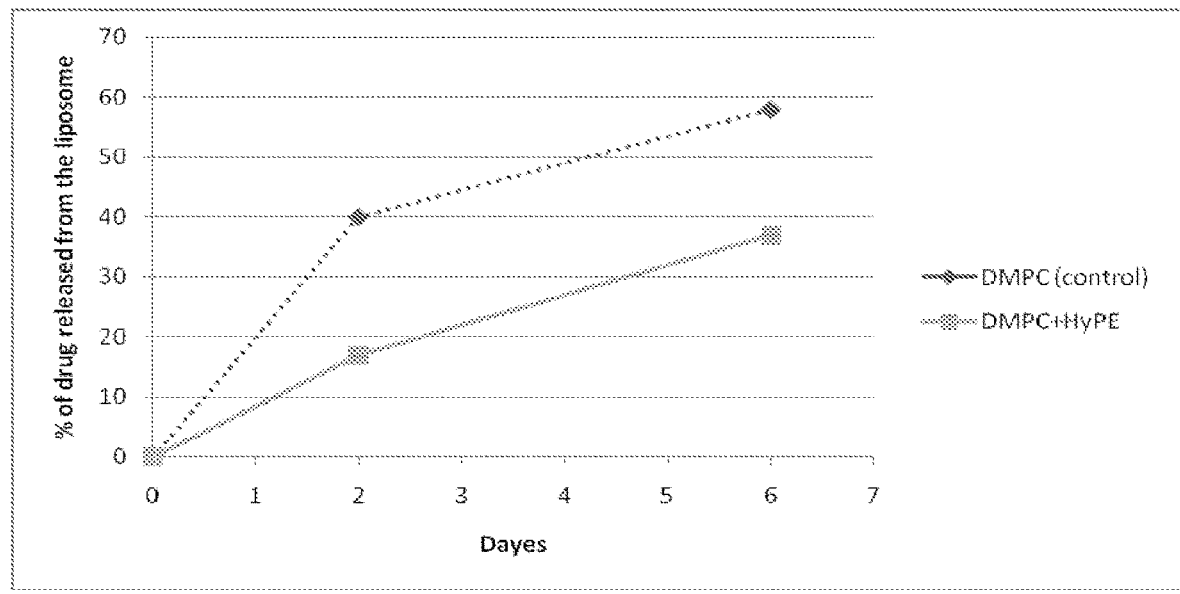
FIG. 5: Stability of liposomes examined by retention of encapsulated drug (Inulin fluorescein=InFl): InFl-containing Liposomes composed of dimyristoyl phosphatidyl-choline (DMPC) with or without Pol-PLI (HyPE) were incubated at 37° C. in blood plasma, and the In-Fl released to the extra-liposomal medium was monitored for 6 days.
Figure 6:
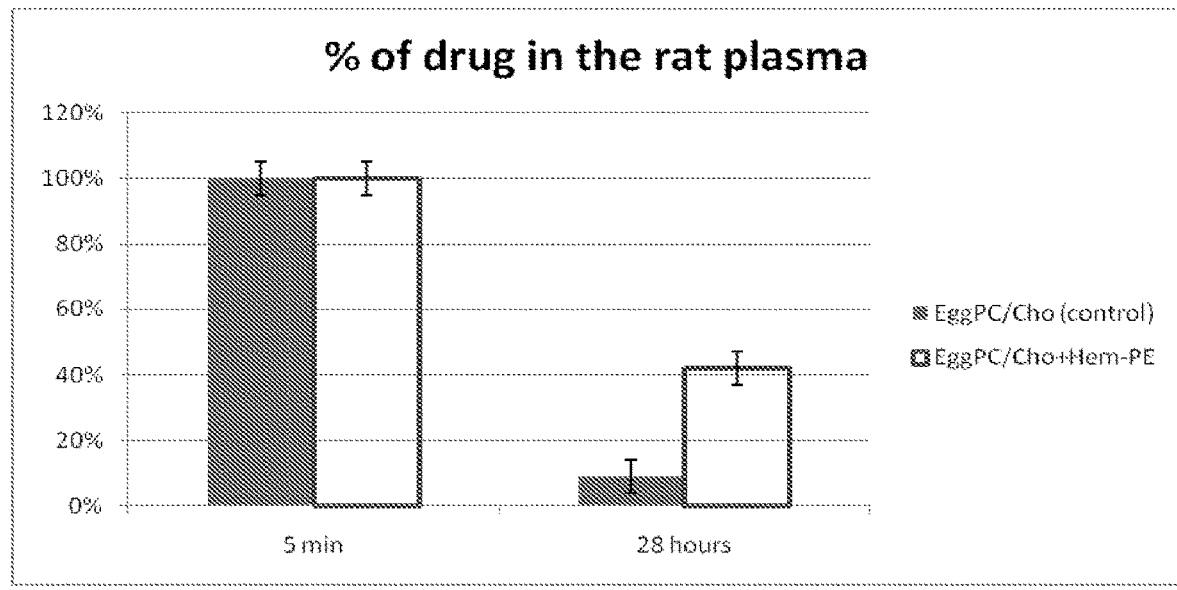
FIG. 6: Effect of Pol-PLI on stability of liposomes in rat blood (in vivo): InFl-containing Liposomes were injected to the tail vein of rats, and the retention of drug in the circulation was monitored for 28 hour, by determination of the drug level in blood samples taken 5 minutes and 28 hours after injection, and expressed as percent of the initial, injected InFl amount. The figure shows that the addition of Hem-PE to the liposomes markedly slowed down the drug release from the liposomes.

Po-L/Lipid NL were markedly more resistant lysis by external phospholipase A2 (the major PL-hydrolyzing enzyme) than control (FIG. 4) or PEGylated (data not shown) nanoliposomes. In addition, the release of encapsulated drug from Po-L/Lipid nanoliposomes (2 days in plasma, 37° C.) was significantly slower than from control nanoliposomes in both in vitro (FIG. 5) and in vivo (FIG. 6) experiments.

These results suggest that Po-L/Lipid NL are suitable for slow release and targeted delivery of drugs, and may have advantages over currently used compositions: Some PoSPL have been developed as anti-inflammatory drugs, and their use thus provides an additional therapeutic benefit, and are composed of natural biodegradable non-immunogenic and non-toxic, as documented in numerous previous studies. In addition, the Po-L provide a platform of compositions that can be modified to be used for differential treatments and organ targeting.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A liposome comprising a lipid bilayer and a polymer-conjugated lipid, wherein said polymer-conjugated lipid is incorporated into said lipid bilayer and wherein said polymer-conjugated lipid is selected from the group consisting of polygeline, a polysaccharide, and a glycosaminoglycan (GAG)-conjugated lipid.

2. The liposome of claim 1, wherein said polymer is polygeline.

3. The liposome of claim 1, wherein said polymer is a polysaccharide.

4. The liposome of claim 3, wherein said polysaccharide is selected from the group consisting of a glycosaminoglycan, chitosan, alginic acid, hetastarch, and dextran.

5. The liposome of claim 4, wherein said polysaccharide is a glycosaminoglycan selected from the group consisting of hyaluronic acid, dermatan sulfate, and heparin.

6. A method of producing a mixed liposome comprising the step of conjugating a lipid with a polymer to form a polymer-conjugated lipid and contacting said polymer-conjugated lipid with a liposome to produce a mixed liposome, wherein said polymer-conjugated lipid is selected from the group consisting of polygeline, a polysaccharide, and a glycosaminoglycan (GAG)-conjugated lipid.

7. The method of claim 6, further comprising the step of isolating said polymer-conjugated lipid prior to said contacting step.

8. A method of delivering a nucleic acid to a subject comprising the step of administering said nucleic acid encapsulated in a liposome of claim 1 to said subject.

9. The method of claim 8, wherein said nucleic acid is delivered to said subject for therapeutic purposes.

10. A method for performing diagnostic imaging in a subject, comprising the step of administering a diagnostic agent encapsulated in a liposome of claim 1 to said subject and imaging said patient.

11. A method for treating, inhibiting or suppressing a pathological condition in a subject, comprising administering to said subject a liposome of claim 1.

12. The method of claim 11, wherein said pathological condition is a cancer.

13. The method of claim 11, wherein said pathological condition is an infection.

14. The method of claim 11, wherein said liposome further comprises a bioactive agent for treating said pathological condition.

15. The method of claim 14, wherein said pathological condition is cancer and said bioactive agent is an anticancer drug.

16. The method of claim 14, wherein said pathological condition is a bacterial infection, a fungal infection, a viral infection, or a parasitic infection and said bioactive agent is an antibacterial drug, an antifungal drug, an antiviral drug or an antiparasitic drug.

17. The method of claim 11, wherein said drug is administered orally, intravenously, intranasally intraocularly, intramuscularly, subcutaneously or topically.

* * * * *